(12) United States Patent  
Baysal et al.

(10) Patent No.: US 8,741,232 B2  
(45) Date of Patent: Jun. 3, 2014

(54) SPECIMEN IMAGING DEVICE AND METHODS FOR USE THEREOF

(71) Applicant: Faxitron Bioptics, LLC, Tucson, AZ (US)

(72) Inventors: Akif Baysal, Tucson, AZ (US); Eric Hutchings, Vail, AZ (US); Brad Jackson, Bartlett, IL (US); Donogh O'Driscoll, Tucson, AZ (US); William Lee, Belfast (GB); Ciaran Purdy, Belfast (GB)

(73) Assignee: Faxitron Bioptics, LLC, Tucson, AZ (US)

( * ) Notice: Subject to any disclaimer, the term of this patent is extended or adjusted under 35 U.S.C. 154(b) by 0 days.

(21) Appl. No.: 13/868,868

(22) Filed: Apr. 23, 2013

(65) Prior Publication Data

US 2014/0065656 A1   Mar. 6, 2014

Related U.S. Application Data

(60) Provisional application No. 61/798,175, filed on Mar. 15, 2013, provisional application No. 61/697,206, filed on Sep. 5, 2012.

(51) Int. Cl.  
*A61B 10/00* (2006.01)

(52) U.S. Cl.  
USPC ............ 422/536; 422/50; 422/500; 422/400; 422/401; 422/560

(58) Field of Classification Search  
USPC ........ 422/63–67, 536, 50, 500, 400–401, 560  
See application file for complete search history.

(56) References Cited

U.S. PATENT DOCUMENTS

| 4,993,056 | A | 2/1991 | Lary |
| 5,156,150 | A | 10/1992 | Lary |
| 5,383,234 | A | 1/1995 | Russell |
| 5,383,472 | A * | 1/1995 | Devlin et al. ................ 600/584 |
| 5,427,742 | A | 6/1995 | Holland |
| 5,664,573 | A | 9/1997 | Shmulewitz |
| 6,353,529 | B1 * | 3/2002 | Cies ....................... 361/679.05 |
| 6,388,262 | B1 | 5/2002 | Alani et al. |
| 6,576,901 | B1 | 6/2003 | Engelhardt |
| 7,715,523 | B2 | 5/2010 | Lafferty |
| 7,784,429 | B2 | 8/2010 | Chiodo |
| 7,951,345 | B2 | 5/2011 | Lary et al. |
| 8,149,506 | B2 * | 4/2012 | Eastman et al. ............. 359/398 |
| 2005/0112032 | A1 | 5/2005 | McCormick |
| 2005/0112758 | A1 | 5/2005 | Archambault et al. |

(Continued)

FOREIGN PATENT DOCUMENTS

| EP | 0532828 B1 | 4/1997 |
| EP | 0730431 B1 | 3/2000 |

(Continued)

*Primary Examiner* — Jyoti Nagpaul  
(74) *Attorney, Agent, or Firm* — Marsh Fischmann & Breyfogle LLP

(57) ABSTRACT

A specimen holding and positioning apparatus operable to substantially non-movably maintain a specimen (e.g., an excised tissue specimen) in a fixed or stable orientation with respect to the apparatus during imaging operations (e.g., x-ray imaging), transport (e.g., from a surgery room to a pathologist's laboratory), and the like for use in facilitating accurate detection and diagnosis of cancers and/or other abnormalities of the specimen.

20 Claims, 20 Drawing Sheets

(56) References Cited

U.S. PATENT DOCUMENTS

| | | |
|---|---|---|
| 2005/0239211 A1 | 10/2005 | Uchihara et al. |
| 2005/0259793 A1 | 11/2005 | Yeo et al. |
| 2007/0116612 A1 | 5/2007 | Williamson, IV |
| 2007/0237684 A1 | 10/2007 | Hansen et al. |
| 2008/0221480 A1 | 9/2008 | Hibner et al. |
| 2010/0075410 A1 | 3/2010 | Desai et al. |

FOREIGN PATENT DOCUMENTS

| | | |
|---|---|---|
| EP | 0625024 B1 | 8/2000 |
| JP | 2001-242152 | 9/2001 |
| JP | 2004-077342 | 3/2004 |
| JP | 2004-146998 | 5/2004 |
| WO | 0019897 | 4/2000 |

\* cited by examiner

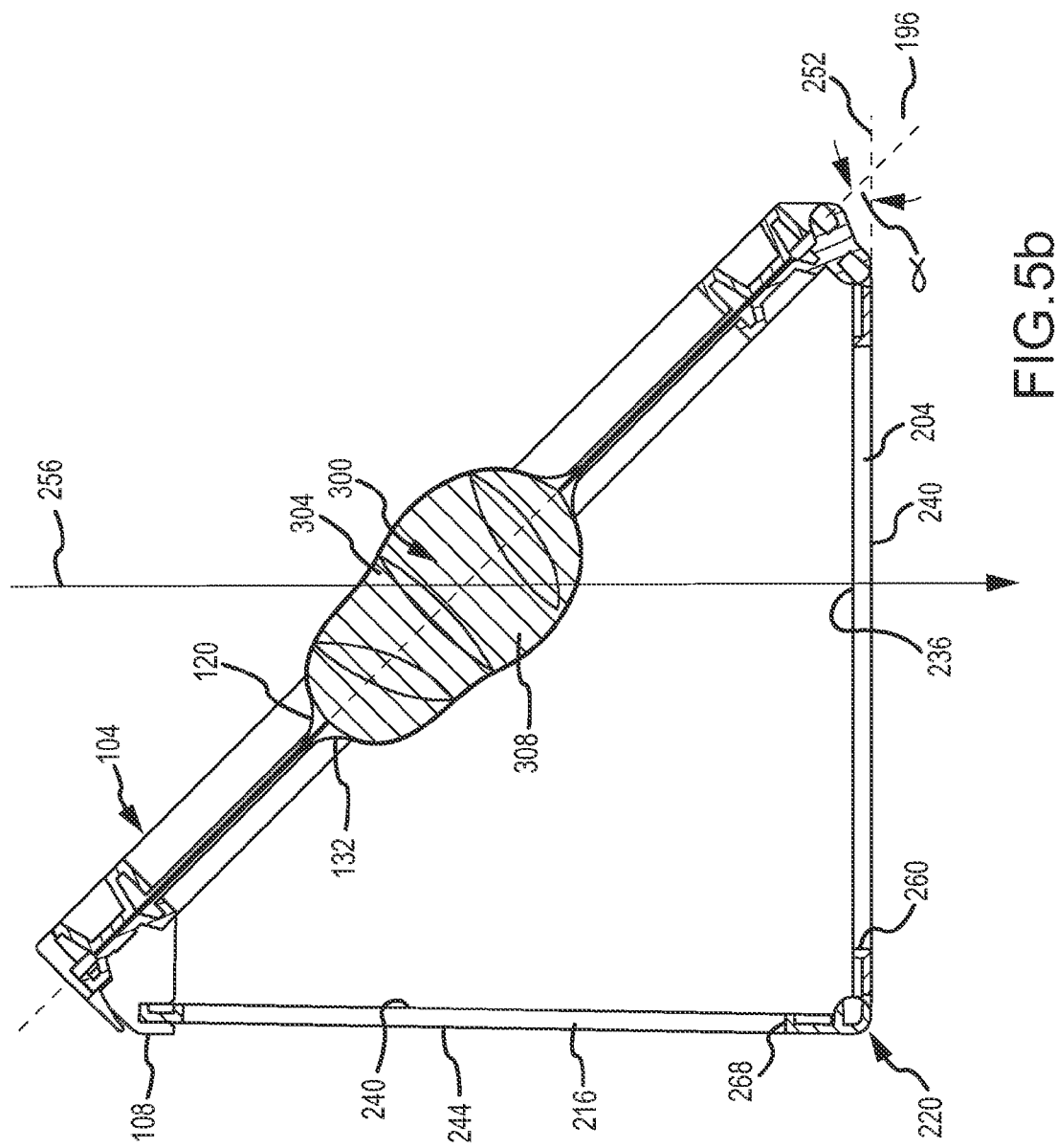

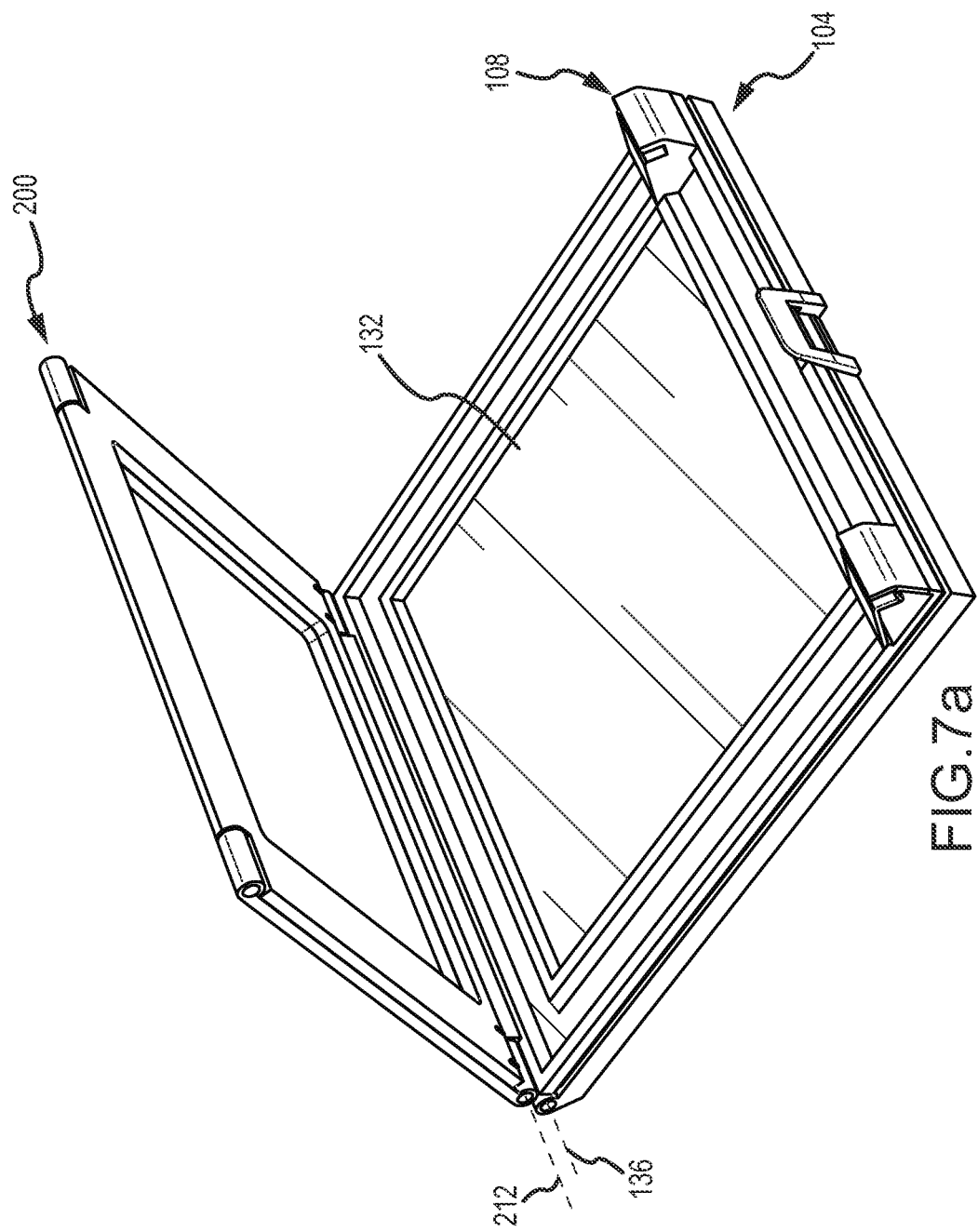

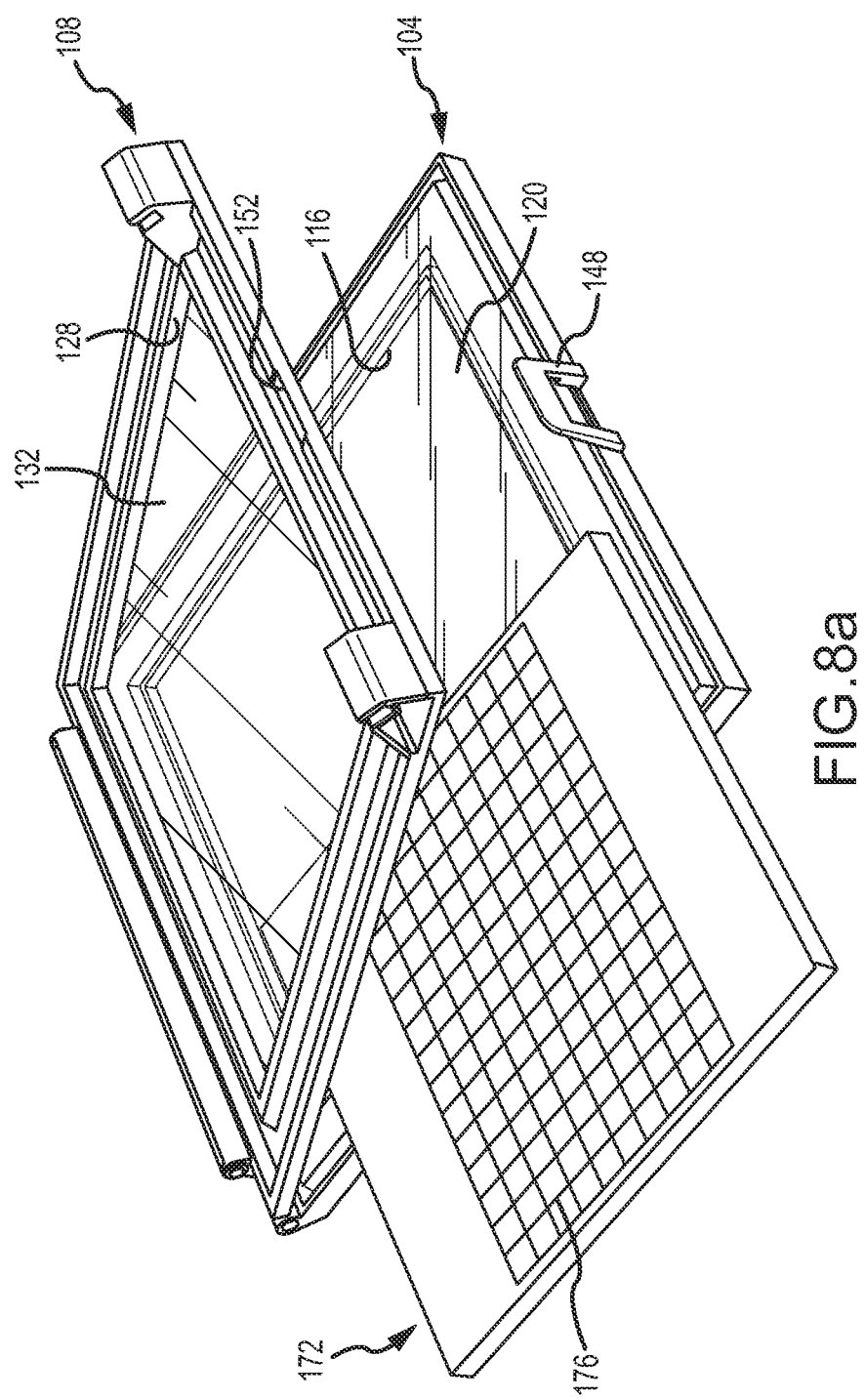

SPECIMEN IMAGING DEVICE AND METHODS FOR USE THEREOF

CROSS-REFERENCE TO RELATED APPLICATIONS

This application claims priority to U.S. Provisional Patent Application No. 61/697,206, filed Sep. 5, 2012, entitled "SPECIMEN IMAGING DEVICE AND METHODS FOR USE THEREOF," and to U.S. Provisional Patent Application No. 61/798,175, filed Mar. 15, 2013, entitled "SPECIMEN IMAGING DEVICE AND METHODS FOR USE THEREOF," which applications are incorporated herein by reference in their entirety.

FIELD OF THE INVENTION

This invention generally relates to tissue specimen analysis and, more particularly, to devices and methods for maintaining an excised tissue specimen in a fixed or stable orientation during imaging and transport to facilitate accurate detection of tissue margins, diagnosis of tissue abnormalities, and the like.

BACKGROUND OF THE INVENTION

Definitive diagnosis of cancers such as breast cancer is typically accomplished through the surgical removal (e.g., biopsy) of the suspicious tissue (e.g., lesion) by a surgeon for further examination by a radiologist and/or pathologist. After a surgeon has appropriately identified a location of a possible lesion, the surgeon proceeds to excise tissue that includes the lesion and then verify that the entirety of the suspicious area is within the margins of the excised tissue. In this regard, a radiologist or the like will often x-ray or otherwise image the excised tissue specimen from multiple views (e.g., orthogonal views) to confirm appropriate tissue margins. In the event that the area of interest is too close or even contacts the tissue margins, the surgeon may need to excise additional tissue.

Once the tissue margins have been confirmed, the surgeon may then appropriately mark or otherwise indicate where on the excised tissue specimen a pathologist should focus during subsequent analysis and diagnosis. For instance, the excised tissue specimen may be positioned flat relative to a location identification member such as a grid or coordinate system (including any appropriate radiopaque lines, indicia, or the like) and then imaged (e.g., x-rayed) so that the grid lines/indicia appear in the resulting image. The surgeon may then appropriately inform the pathologist the location(s) of the most suspicious areas in the resulting image (e.g., by providing coordinates, marking directly on the image, etc.). The resulting image and excised tissue specimen may then be sent to the pathologist for performing a diagnostic procedure and providing a diagnostic opinion.

During all or most of the period between tissue specimen excision up to and including pathologist diagnosis, it is important for the tissue specimen to remain in a substantially constant shape and/or a substantially undisturbed position with respect to some particular reference point or device (e.g., relative to a tray or carrier used to transport the specimen). For instance, reshaping of the tissue specimen (e.g., compressing, folding, etc.) between the taking of first and second orthogonal images (e.g., for use in tissue margin detection) can make accurate tissue margin analysis difficult or even impossible. As another example, the pathologist may have difficulty reconciling the locations on the resulting image identified by the surgeon or radiologist and corresponding locations on the actual excised tissue specimen and possibly leading to an inaccurate diagnosis in the event that the tissue specimen is moved relative to the grid or coordinate system during transport from the surgeon or radiologist to the pathologist.

SUMMARY OF THE INVENTION

The present disclosure is directed to devices and methods (i.e., utilities) for maintaining an excised tissue specimen in a fixed or stable orientation during imaging and transport to facilitate accurate detection of tissue margins, diagnosis of tissue abnormalities, and the like. In one regard, the disclosed utilities may be used to facilitate accurate and efficient multi-axis imaging (e.g., orthogonal imaging) of a tissue specimen. In another regard, the disclosed utilities may be additionally used to facilitate substantially horizontal or flat imaging of the tissue specimen and a corresponding at least partially radiopaque grid or coordinate system to allow a surgeon or radiologist to accurately identify suspicious locations or areas in the excised tissue specimen to be subsequently analyzed by a pathologist or the like. In a further regard, the disclosed utilities may be additionally used to facilitate transport of the excised tissue specimen between two or more locations in a manner at least substantially free of changes in position or orientation of the tissue specimen relative to a reference location or device. Still further, the disclosed utilities may be used to substantially limit deformation and/or changes in shape of the specimen during imaging, transport, and the like.

In one aspect, an apparatus for use in positionably retaining a tissue specimen is disclosed including first and second positioning members that are broadly configured to retain and suspend a tissue specimen therebetween for use in imaging, transport and diagnosis of the tissue specimen. More specifically, the first positioning member includes a first frame member having a first opening therein spanned by a first at least partially elastically deformable sheet member (e.g., made of a radiolucent material), and the second positioning member includes a second frame member having a second opening therein spanned by a second at least partially elastically deformable sheet member (e.g., made of a radiolucent material). The first and second frame members are fixably positionable relative to each other (e.g., via respective first and second connection elements of the first and second positioning members) to allow the first and second at least partially deformable sheet members to retain a tissue specimen therebetween and suspend the tissue specimen within the first and second openings. The apparatus may be adapted for use with an imaging signal, where each of the first and second sheet members may be configured to at least partially transmit the imaging signal therethrough.

In one arrangement, the apparatus may include a prop (e.g., support, brace, etc.) extendable from at least one of the first and second positioning members that is positionable on a support surface and configured to position a reference plane extending between the first and second sheet members at one or more desired angles or orientations relative to the support surface. For instance, imagine the first and second positioning members are fixably positioned relative to each other and a tissue specimen is retained and suspended between the first and second sheet members so that the reference plane extends between the first and second sheet members and through the tissue specimen. In this case, the prop may be used to position the reference plane at a first orientation relative to the support surface so that a first image may be taken along a first axis through the tissue specimen. The prop may then be used to position the reference plane at a second orientation relative to the support surface (e.g., pivoted 90° from the first orientation) so that a second image may be taken along a second axis through the tissue specimen (e.g., orthogonal to the first axis), such as for use in tissue margin detection and the like.

The prop may include at least a first prop member that is interconnectable to at least one of the first and second positioning members and/or fixably positionable relative to at least one of the first and second positioning members. For instance, the prop may be configured to position the reference plane at an acute angle relative to the support surface (e.g., where the acute angle is one of the desired angles). The prop may in some arrangements also include a second prop member interconnectable to the first prop member to position the reference plane at the acute angle (or other angles) relative to the support surface. For instance, the first and second (and/or additional) prop members may be angularly positionable (e.g., pivotably attachable) relative to each other (e.g., via respective hinge elements) to obtain one or more desired angles between the reference plane and the support surface. In one arrangement, one or both of the first and second prop members may be movably and/or removably interconnectable to the first and/or second positioning members (e.g., to obtain one or more desired angles, to allow for collapsing of the prop against the positioning members to facilitate storage and/or transport of the apparatus, to facilitate flat imaging of the specimen, and/or the like).

In another arrangement, the apparatus may include or be usable with a grid member (e.g., sheet, board, etc.) having a series of grid lines (e.g., at least partially radiopaque grid lines) across at least one surface thereof for use in imparting the grid lines into resulting images of the tissue specimen (e.g., horizontal or flat images of the that may be used by a surgeon or radiologist to accurately indicate areas of interest on the specimen). In one embodiment, the grid member may be in the form of a rigid board (e.g., low attenuating or radiolucent material such as foam) that may be placed inside of the apparatus over one of the first and second sheet members. Upon placing a tissue specimen onto the grid board, the first and second positioning members may be fixably positioned relative to each other (i.e., the apparatus may be closed) so as to at least partially deform the first and second sheet members about the tissue specimen and the grid board and thereby suspend the tissue specimen and grid board within the first and second openings of the first and second positioning members. Stated differently, each of the tissue specimen and the grid board may be allowed to "float" within the first and second openings relative to the first and second frame members of the first and second positioning members as the apparatus is being closed. Allowing the grid board to at least partially give or yield by way of one of the first and second sheet members as the tissue specimen is being urged against the grid board (during closure of the apparatus) advantageously reduces the degree to which the tissue specimen may otherwise deform upon closing of the apparatus.

For some types of tissue specimens, providing at least some amount of compression of the specimen during orthogonal imaging may increase the clarity of particular portions of the resulting images. In this regard, one variation disclosed herein includes inserting a rigid board free of grid lines into the apparatus so as to float within the first and second openings (during closure of the apparatus) to at least partially compress the tissue specimen during orthogonal imaging (e.g., in conjunction with the prop disclosed herein). For instance, the first and second positioning members may be separated, the board may be placed over one of the sheet members, the specimen may be placed on top of the board, and the first and second positioning members may be brought together and secured so as to close the apparatus and deform the first and second sheet members about the specimen and board. The prop may be appropriately deployed for use in orthogonal imaging of the specimen.

In another embodiment, the grid member may be removably securable to one of the first and second frame members so as to span the first or second opening. For instance, the grid member may be disposable adjacent one end of the first opening and the first sheet member may be disposable adjacent an opposing end of the first opening such that the grid member and first sheet member may overlap one another and be spaced from each other. As a result, the grid member may function to impart grid lines into a resulting image of the specimen substantially free of physically deforming or distorting the specimen (e.g., because the portion of the specimen deforming the first sheet member while being retained by the first sheet member would be substantially received in the first opening rather than substantially contacting the grid member).

In another aspect, an apparatus for use in positionably retaining a tissue specimen is disclosed including a first positioning member having a first frame member and a first imaging zone through the first frame member and a second positioning member having a second frame member and a second imaging zone through the second frame member, where the first and second frame members are fixably positionable to allow the first and second imaging zones to hold a tissue specimen therebetween. The apparatus includes a prop (e.g., support, brace, etc.) extendable from at least one of the first and second positioning members that is positionable on a support surface and configured to position a reference plane extending between the first and second sheet members (when the first and second positioning members are fixably positioned relative to each other) at one or more desired angles or orientations relative to the support surface.

In one arrangement, the first and second imaging zones may include respective first and second at least partially elastically deformable members (e.g., radiolucent members) that are respectively configured to deform around first and second portions of a tissue specimen when the first and second frame members are fixedly positioned relative to each other. For instance, the first and second imaging zones may respectively include first and second cavities that are respectively configured to receive the first and second portions of the tissue specimen (e.g., to limit compression or deformation of the tissue specimen when the tissue specimen is retained between the first and second imaging zones).

In another aspect, a method for use in tissue abnormality diagnosis includes excising a tissue specimen from a patient, substantially fixing and retaining the tissue specimen within a positioning apparatus against movement relative to the positioning apparatus, and performing one or more imaging operations on the tissue specimen while the tissue specimen is substantially fixed and retained within the positioning apparatus.

As an example, the fixing and retaining operation may include locating the excised specimen between a pair of sheet members (e.g., films, layers) of the positioning apparatus, advancing at least one of the sheet members towards the other of the sheet members, and elastically deforming the first and second sheet members about opposing portions of the specimen to capture the specimen between the sheet members. In one arrangement, the first and second sheet members may contact first and second opposing portions of the specimen so that the opposing portions of the specimen are received within the cavities or openings of the frame members. In the context of horizontal imaging, for instance, a grid member may be placed over one of the sheet members (e.g., across at least a portion of one of the first and second openings). In this arrangement, advancing at least one of the sheet members towards the other of the sheet members may cause one of the sheet members to elastically deform about and contact one of the opposing portions of the specimen and the other of the sheet member to elastically deform about and contact the grid member. In either case, the first and second sheet members may be considered to be elastically deformed "about" (e.g., so as to surround) the opposing portions of the specimen.

Once the specimen has been captured between the sheet members, the frame members may be removably connected to each other (e.g., via corresponding respective connection members) to maintain the specimen (and possibly a grid member) in a fixed and retained position within and relative to the positioning apparatus. In one arrangement, the sheet members may also be configured to substantially limit deformation or shape changes of the specimen. For instance, one or more properties of the material(s) of the sheet members (e.g., modulus of elasticity) and/or dimensions of the sheet members (e.g., thickness) may be selected so that the sheet members are substantially precluded from deforming or changing the natural shape of the specimen while at the same time substantially restricting the specimen from movement or reorientation relative to the apparatus.

In one arrangement, a radiologist or the like may perform multi-axis imaging operations on the excised tissue specimen to verify that the surgeon has obtained the appropriate tissue margins in the specimen. For instance, the method may include orienting the positioning apparatus relative to a support surface (e.g., so that a reference plane passing through the specimen is at a particular angle relative to the support surface, such as 45°) to allow the radiologist to obtain an image along a first axis through the tissue specimen. The method may then include reorienting the positioning apparatus relative to the support surface (e.g., via tipping the positioning apparatus 90° relative to the support surface while the tissue specimen remains in the same position with respect to the apparatus) to obtain an image along a second axis through the tissue specimen. The resulting first and second images may then be used to verify tissue margins or the like.

In another arrangement, a substantially horizontal or flat (e.g., with respect to a support surface) imaging operation on the tissue specimen may be performed to obtain an image that may be used by the surgeon to indicate suspicious areas (e.g., areas of interest) on or in the tissue specimen). As discussed above, the method may include inserting and fixing a grid sheet or member having a series of radiopaque grid lines thereon into or onto the positioning apparatus and then imaging the tissue specimen so that the grid lines appear in the resulting image. The surgeon may then utilize the grid lines or coordinates to indicate areas of interest on the tissue specimen to be analyzed by a pathologist or the like. The method may also include transporting the tissue specimen from a first location (e.g., of the surgeon and/or radiologist) to a second location (e.g., of a pathologist) in a manner substantially free of changing a position of the tissue specimen relative to the grid member (e.g., to allow the pathologist to be able to view the areas of interest on the image as identified by the surgeon and then accurately locate corresponding locations on the actual tissue specimen).

Various refinements may exist of the features noted in relation to the various aspects. Further features may also be incorporated in the various aspects. These refinements and additional features may exist individually or in any combination, and various features of the aspects may be combined. In addition to the exemplary aspects and embodiments described above, further aspects and embodiments will become apparent by reference to the drawings and by study of the following descriptions.

DESCRIPTION OF THE DRAWINGS

For a more complete understanding of the present invention and further advantages thereof, reference is now made to the following Detailed Description, taken in conjunction with the drawings, in which:

FIG. 5*b* is a cross-sectional view through the apparatus of FIG. 5*a* and showing a first image being taken along a first axis through the specimen.

FIGS. 7*a*-7*b* are perspective views of the specimen holding apparatus illustrating a process of removing the prop from the apparatus.

FIG. 8*a* is a perspective view of the specimen holding apparatus similar to that in FIG. 2 but illustrating a removable radiopaque grid member that may be used with the apparatus, according to one embodiment.

DETAILED DESCRIPTION

Reference will now be made to the accompanying drawings, which assist in illustrating the various pertinent features of the various novel aspects of the present disclosure. In this regard, the following description is presented for purposes of illustration and description. Furthermore, the description is not intended to limit the inventive aspects to the forms disclosed herein. Consequently, variations and modifications commensurate with the following teachings, and skill and knowledge of the relevant art, are within the scope of the present inventive aspects.

Figure 1:
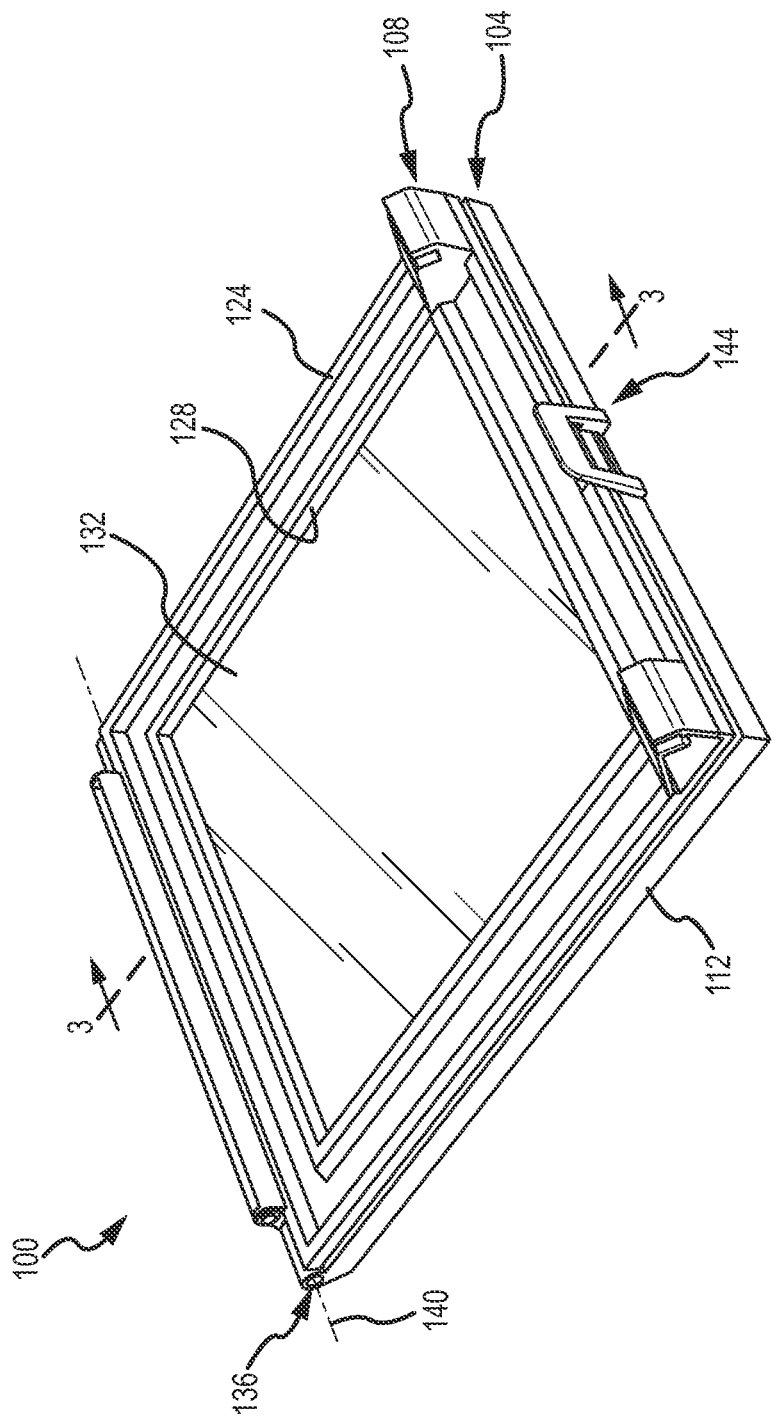
FIG. 1 is a perspective view of a specimen holding apparatus according to one embodiment, in a closed orientation.
Figure 2:
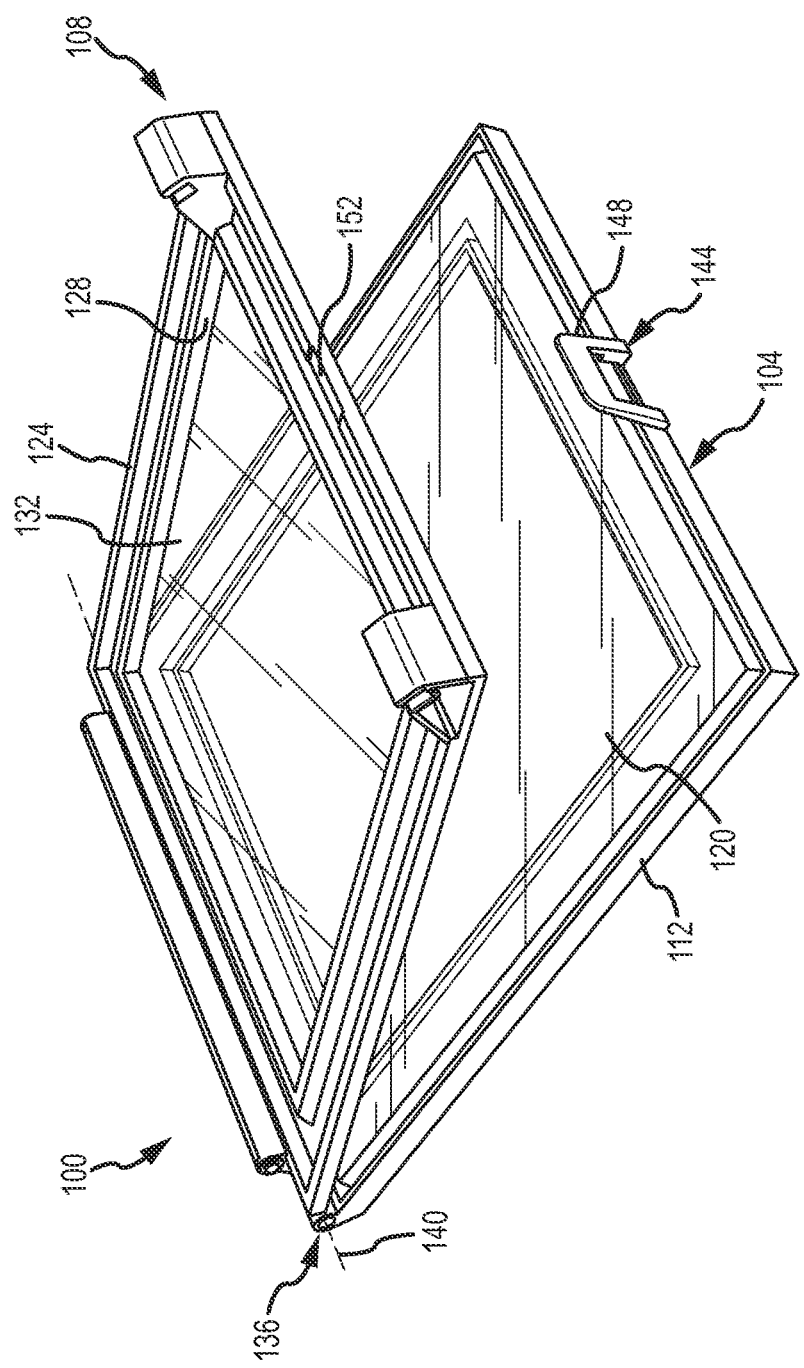
FIG. 2 is a perspective view of the specimen holding apparatus of FIG. 1, in an open orientation.
Figure 3:
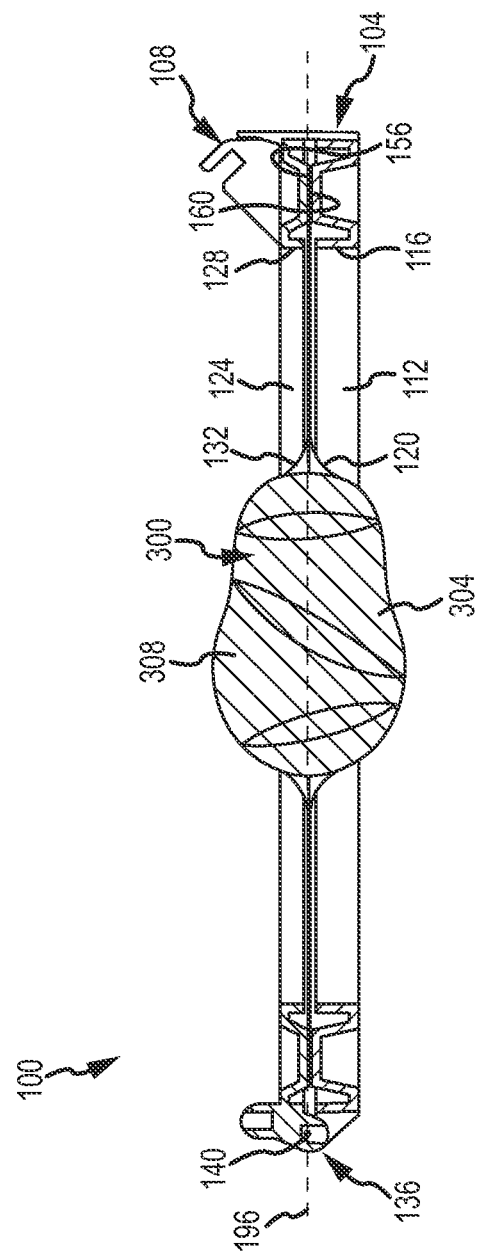
FIG. 3 is a cross-sectional view of the specimen holding apparatus along the line 3-3 of FIG. 1, and with a specimen retained within the apparatus.

With initial respect to FIGS. 1-3, a specimen holding and positioning apparatus 100 is disclosed that is operable to maintain a specimen 300 (e.g., an excised tissue specimen) in a fixed or stable orientation with respect to the apparatus 100 during imaging operations (e.g., x-ray imaging), transport (e.g., from a surgery room to a pathologist's laboratory), and the like to facilitate the accurate detection and diagnosis of cancers and/or other abnormalities of the specimen 300. Broadly, the apparatus 100 includes a first positioning member 104 movably interconnected to a second positioning member 108, where the first and second positioning members 104, 108 are designed to non-movably (i.e., with respect to the apparatus 100) retain the specimen 300 therebetween upon securement of the first and second positioning members 104, 108 to each other.

As shown, the first positioning member 104 may include a first frame member 112, a first cavity or opening 116 extending through the first frame member 112, and a first sheet member 120 interconnected to or retained by the first frame member 112 and spanning (e.g., extending across at least a substantial entirety of) the first opening 116. The second positioning member 108 may include a second frame member 124, a second cavity or opening 128 extending through the second frame member 124, and a second sheet member 132 interconnected to or retained by the second frame member 124 and spanning (e.g., extending across at least a substantial entirety of) the second opening 128.

The apparatus 100 may have one or more features that allow for fixable positioning of the first and second frame members 112, 124 to allow for substantial non-movable retaining of the specimen 300 between the first and second sheet members 120, 132 and suspension of the specimen 300 within the first and second openings 116, 128. In one arrangement, the apparatus 100 may include any appropriate hinge mechanism 136 that allows for pivotal movement between the first and second positioning members 104, 108 about a pivot axis 140. For instance, the first and second positioning members 104, 108 may include respective first and second hinge elements (not shown) that are secured to or at least partially form the hinge mechanism 136. The hinge mechanism 136 may allow for relative positioning between the first and second sheet members 120, 132 between a number of positions, such as at least an open position (e.g., as in FIG. 2) that allows for placement of the tissue specimen 300 between the first and second sheet members 120, 132 and a closed position (e.g., as in FIGS. 1 and 3) that holds the tissue specimen 300 between the first and second sheet members 120, 132 against movement relative to the first and second frame members 112, 124.

Additionally or alternatively, the apparatus 100 may also include any appropriate securing mechanism 144 that is operable to removably secure the apparatus 100 in the closed position as in FIGS. 1 and 3 (e.g., to fixedly position the first and second frame members 112, 124 relative to each other). As one example, the first positioning member 104 may include a first connection member such at least one flexible or resilient tab 148 that is configured to snap into, snap past or otherwise engage with a corresponding second connection member such as an opening 152, ledge or the like on the second positioning member 108. The tab 148 may be lifted or otherwise moved away from the opening 152 to allow for separation of the first and second positioning members 104, 108. As another example, the first positioning member may include one or more openings (not shown) in the first frame member 112 that are each configured to matingly receive a second connection member such as a respective post (not shown) extending from the second frame member 124 of the second positioning member 108.

In one arrangement, the posts may be press fit into the openings; in another arrangement, the posts may be snapped or deformed into the openings. For instance, the securing mechanism 144 may be configured so that upon application of a particular separation force to the apparatus (i.e., a force tending to separate the first and second positioning members 104, 108, such as a force generated via a user grasping one of the first and second frame members 112, 124 and pulling on the other of the first and second frame members 112, 124), the first and second frame members 112, 124 may be at least partially separated and the apparatus 100 opened (or moved into an open position or configuration) to allow for access to or placement of the tissue specimen 300 between the first and second sheet members 120, 132.

Each of the first and second sheet members 120, 132 may be configured to at least partially transmit an imaging signal therethrough to allow for imaging of the specimen 300. For instance, each of the first and second sheet members 120, 132 may be constructed of any appropriate radiolucent material such as a polyurethane film or the like. Furthermore, the first and second sheet members 120, 132 may be at least partially elastically deformable at least partially around respective first and second portions 304, 308 of the specimen 300 so as to substantially non-movably (e.g., relative to the apparatus 100) retain the specimen 300 between the first and second sheet members 120, 132 and within the first and second openings 116, 128 when the first and second frame members 112, 124 are fixably positioned relative to each other.

The material properties (e.g., modulus of elasticity) and/or dimensions (e.g., thickness) of each of the first and second sheet members 120, 132 may be selected to suspend and retain the specimen 300 within the first and second openings 116, 128 against movement with respect to the first and second frame members 112, 124. In one arrangement, the material properties and/or dimensions of the first and second sheet members 120, 132 may be selected or configured to substantially inhibit deformation of the specimen 300 from its natural shape and dimensions by the first and second sheet members 120, 132 while still allowing the first and second sheet members 120, 132 to retain the specimen 300 against movement relative to the apparatus 100. As just one example, the thickness of one or both of the first and second sheet members 120, 132 may be greater than about 0.001", such as greater than about 0.002". As another example, the thickness of one or both of the first and second sheet members 120, 132 may be less than about 0.008", such as less than about 0.006".

Furthermore, the first and second sheet members 120, 132 may be respectively secured to the first and second frame members 112, 124 so that the first and second sheet members 120, 132 are substantially parallel and adjacent to each other when the apparatus 100 is in the closed position (e.g., except for those portions of the first and second sheet members 120, 132 in contact with the specimen 300). As an example, the first and second frame members 112, 124 may have respective first and second mounting surfaces 156, 160 respectively surrounding the first and second openings 116, 128 that are configured to receive the first and second sheet members 120, 132. For instance, the first and second sheet members 112, 124 may be placed over the first and second openings 116, 128 and appropriately secured to the first and second mounting surfaces 156, 160 of the first and second frame members 112, 124 (e.g., via adhesives, heat sealing, and/or the like).

As discussed previously, it is often desirable or necessary to image a specimen 300 along a number of different axes through the specimen 300. For instance, a particular excised tissue specimen may be imaged along first and second different axes through the specimen and the resulting first and second images may be analyzed to verify that any appropriate or required tissue margins have been satisfied. However, previous manners of positioning tissue specimens for obtaining multi-axis images have been deficient in a number of regards such as difficulty of use, movement and/or deformation of the specimen between the first and second imaging steps, and the like.

Figure 5A:
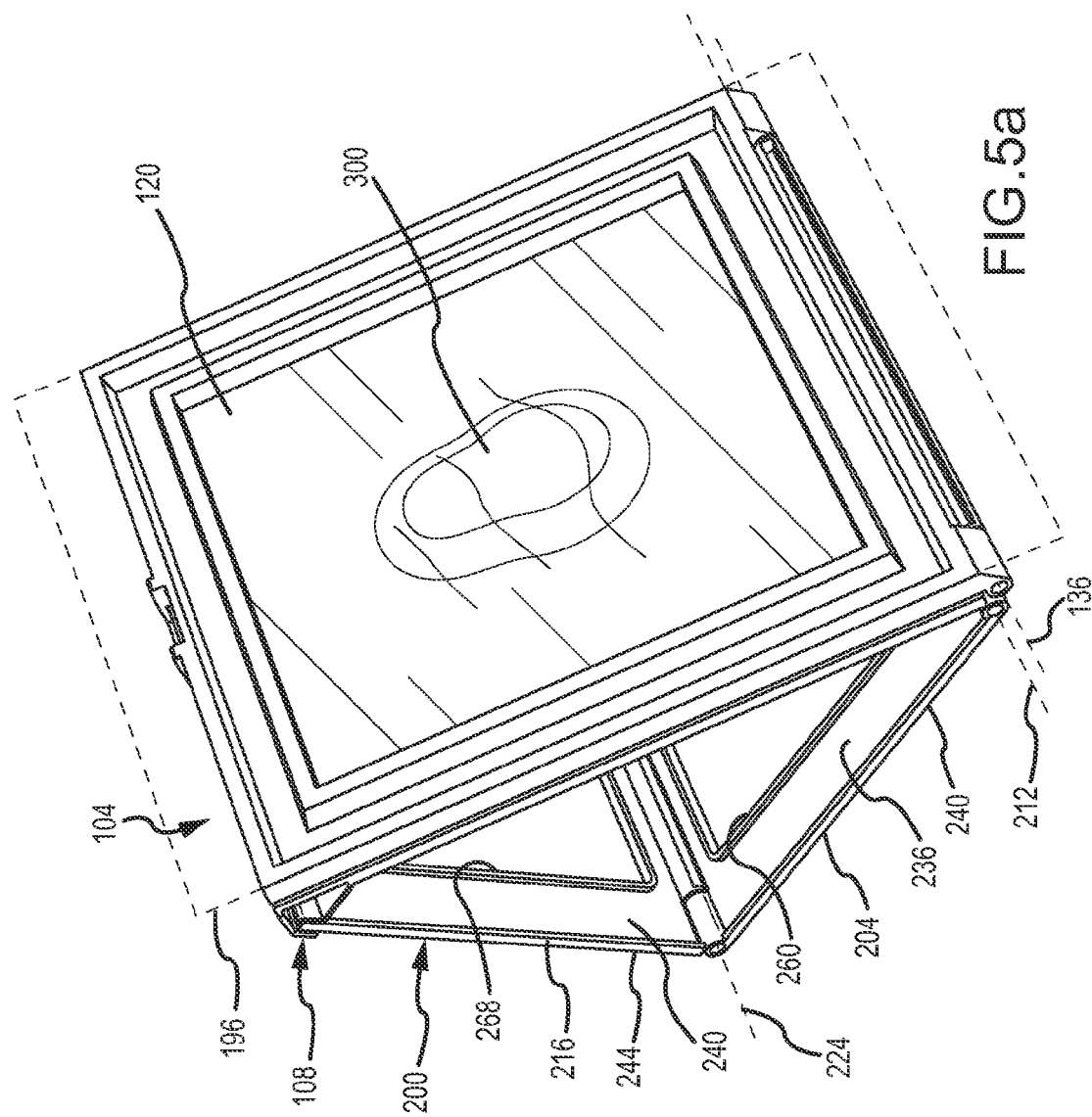
FIG. 5*a* is a perspective view of the specimen holding apparatus of FIG. 4*f* in a first orientation.
Figure 6A:
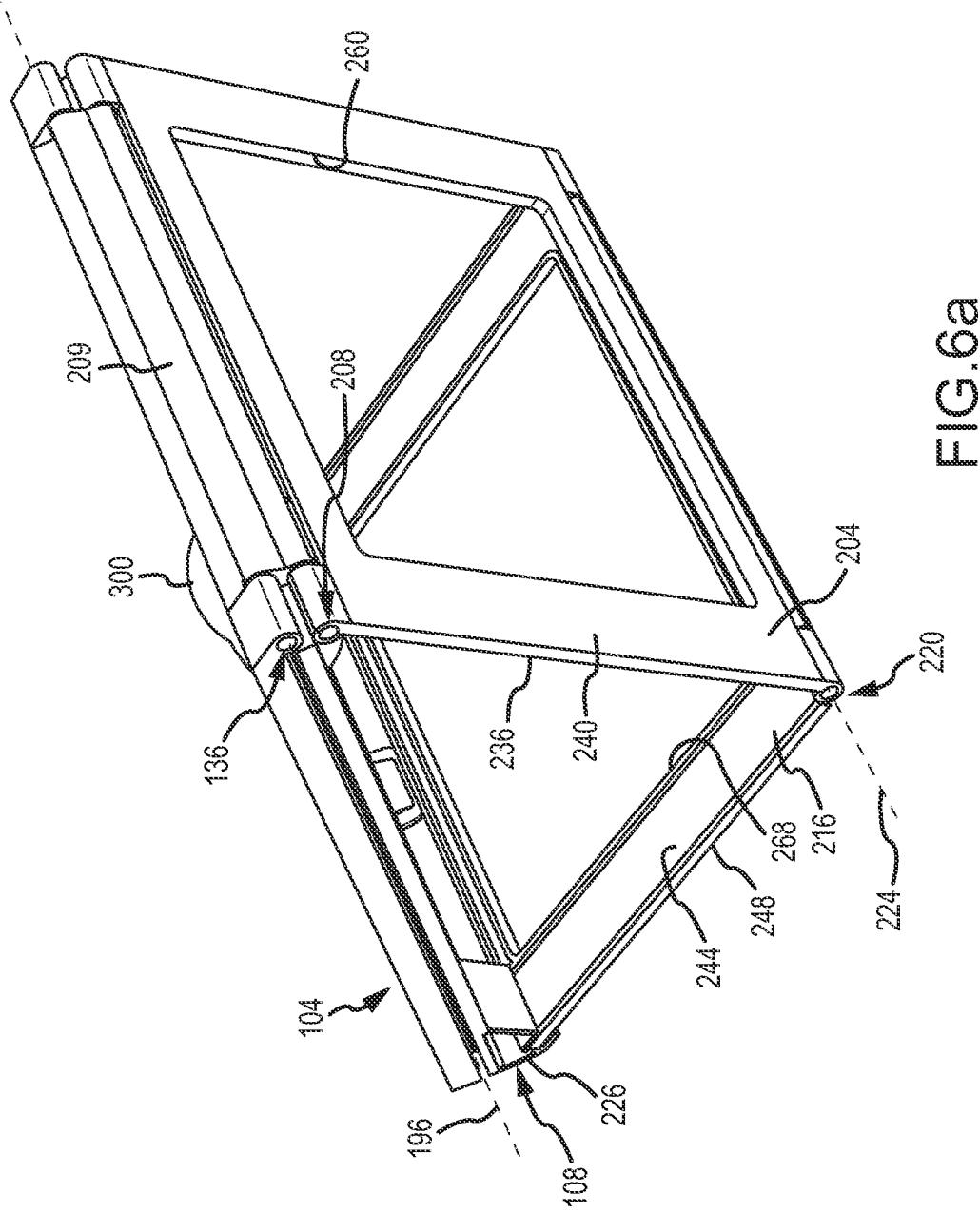
FIG. 6*a* is a perspective view of the specimen holding apparatus of FIG. 4*f* in a second orientation.
Figure 6B:
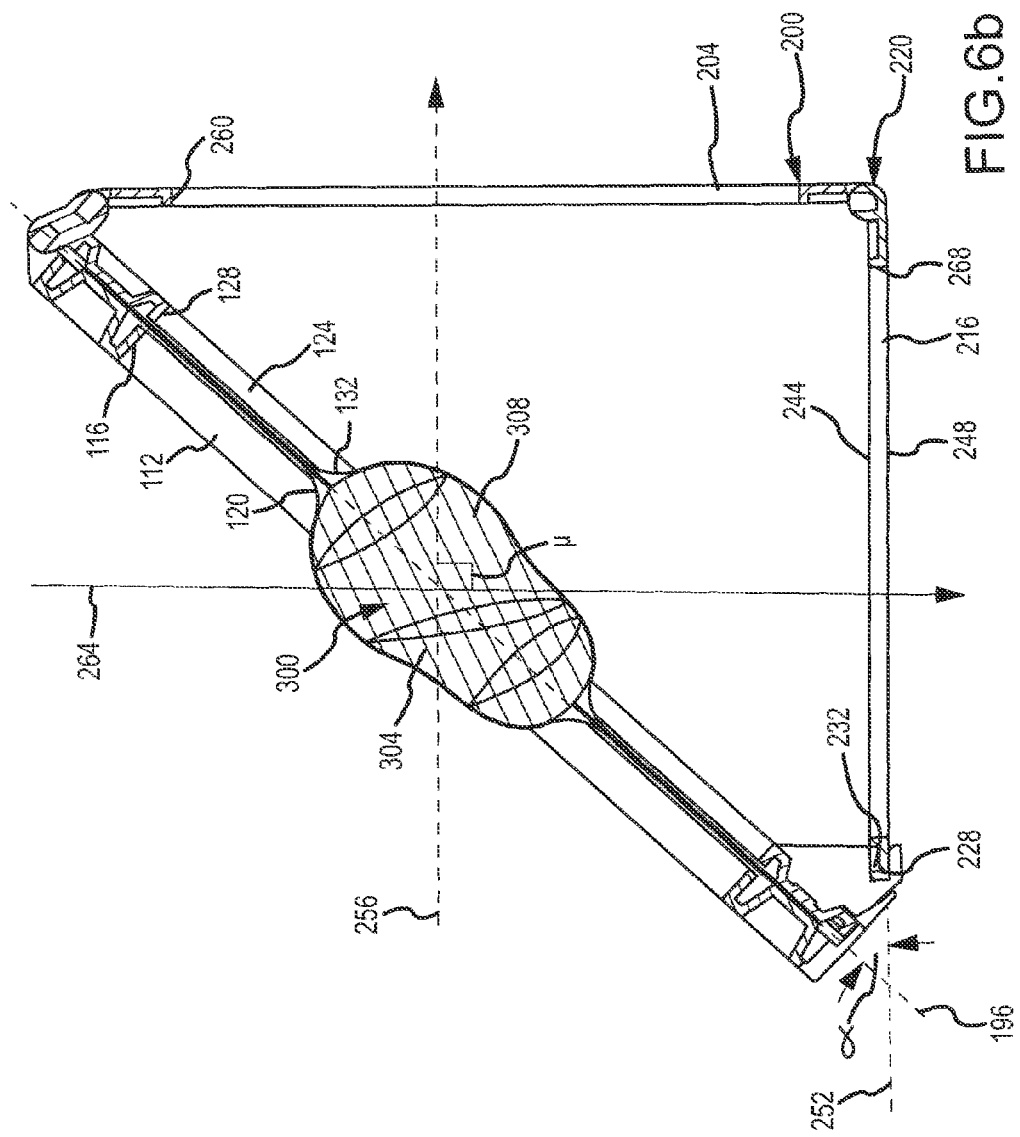
FIG. 6*b* is a cross-sectional view through the apparatus of FIG. 6*a*, but showing a second image being taken along a second axis through the specimen.

In this regard, and turning briefly to FIG. 5a, the apparatus 100 may include a support member or prop 200 extendable from at least one of the first and second positioning members 104, 108 and that is designed to efficiently orient the first and second positioning members 104, 108 (and thus a tissue specimen 300 retained between the first and second members 120, 132) at one or more desired positions or orientations, such as for use in obtaining one or more images of the specimen 300 along a number of different axes through the specimen 300. More specifically, the prop 200 may be configured to position a reference plane 196 (also see FIGS. 3 and 5b) extending between the first and second sheet members 120, 132 and through the specimen 300 (when the apparatus 100 is in the closed position) at one or more desired angles and/or orientations relative to a support surface (not shown) on which the apparatus 100 is disposed (e.g., such as at an acute angle as shown in FIGS. 5a-5b) as will be discussed in more detail below.

Figure 4A:
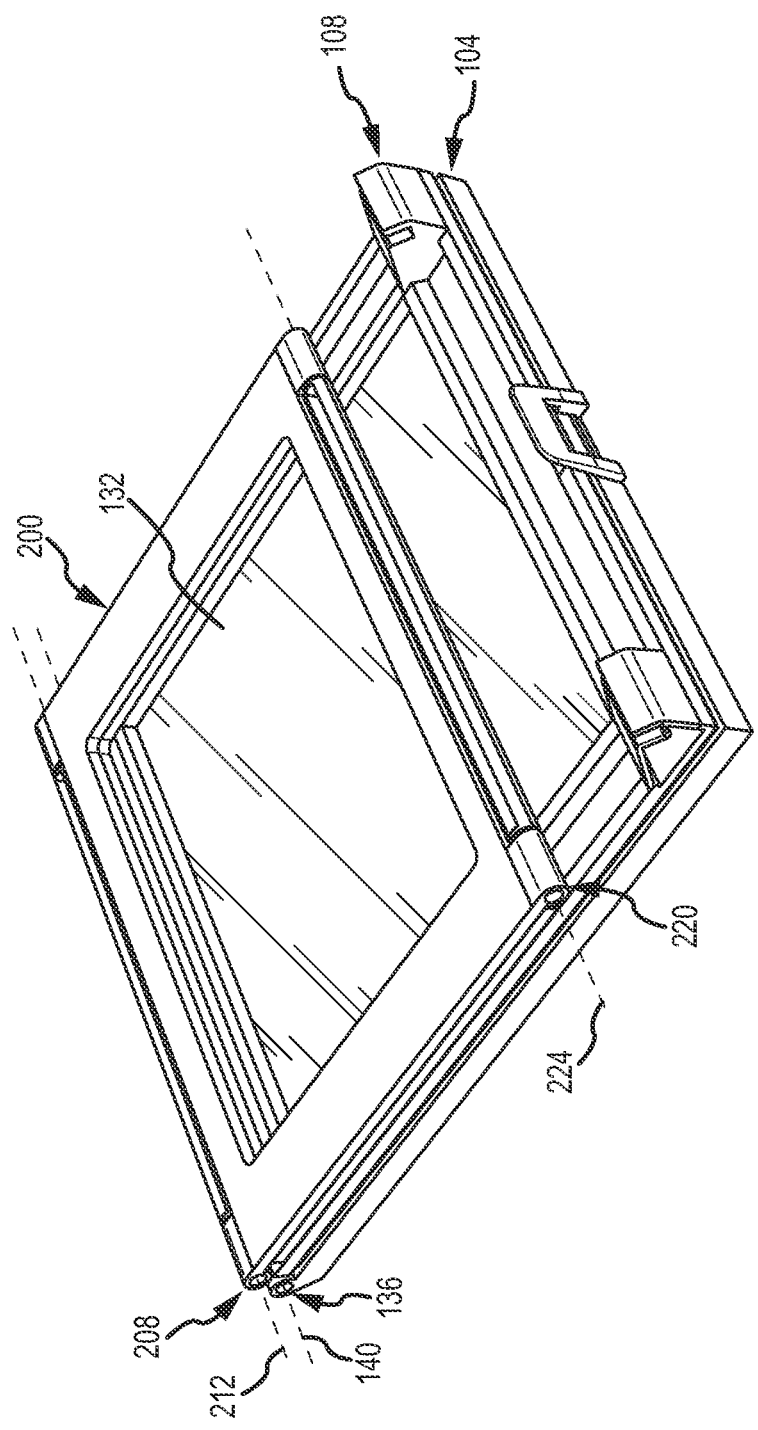
FIGS. 4*a*-4*f* are perspective views of the specimen holding apparatus similar to FIG. 1, but showing a removably attachable prop or support member that may be used to position or orient the specimen holding apparatus at one or more desired angles relative to a support surface, where the figures illustrate various successive positions of the prop from a collapsed position as shown in FIG. 4*a* up to a deployed position as shown in FIG. 4*f*.
Figure 4B:
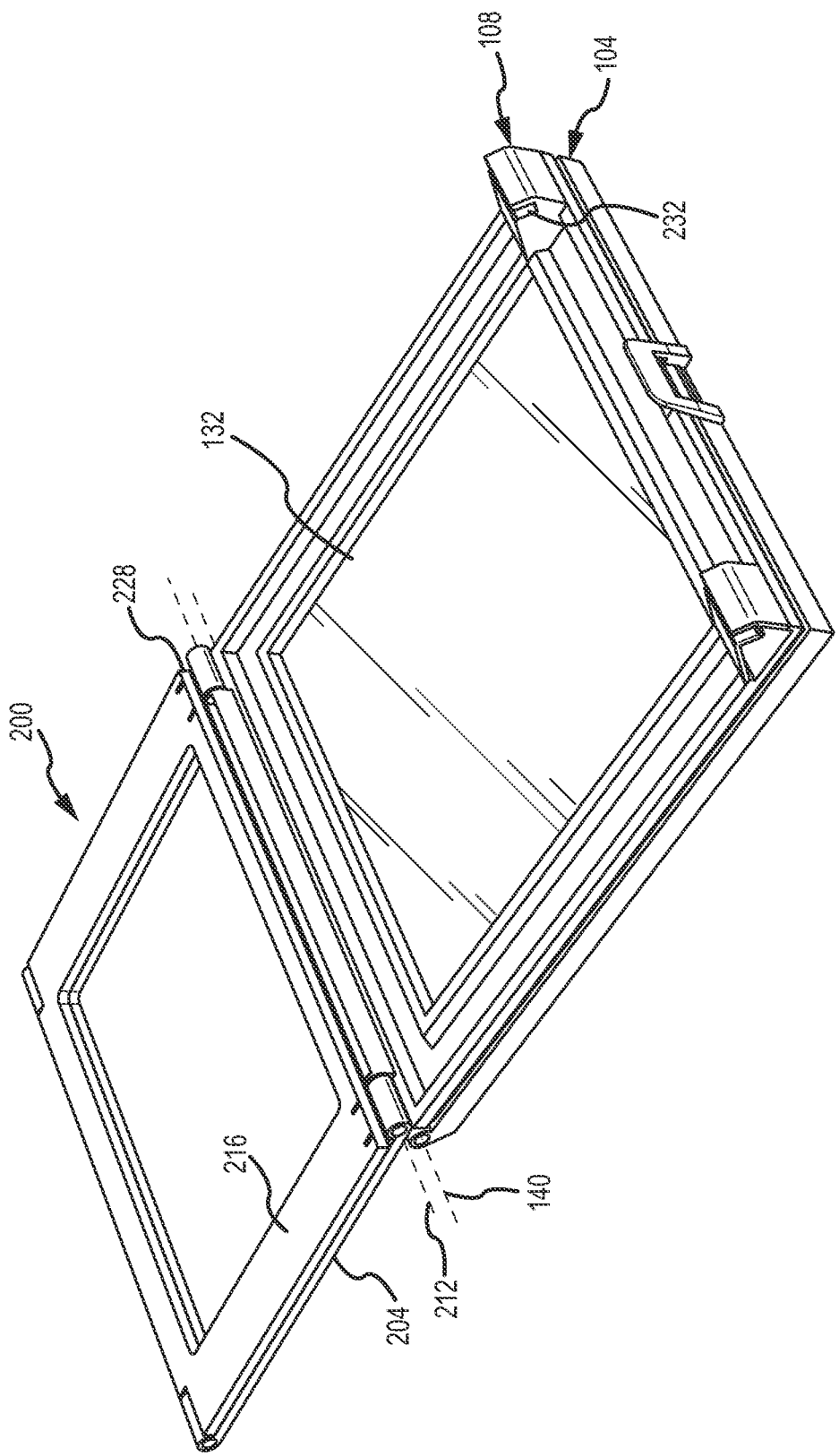
Figure 4C:
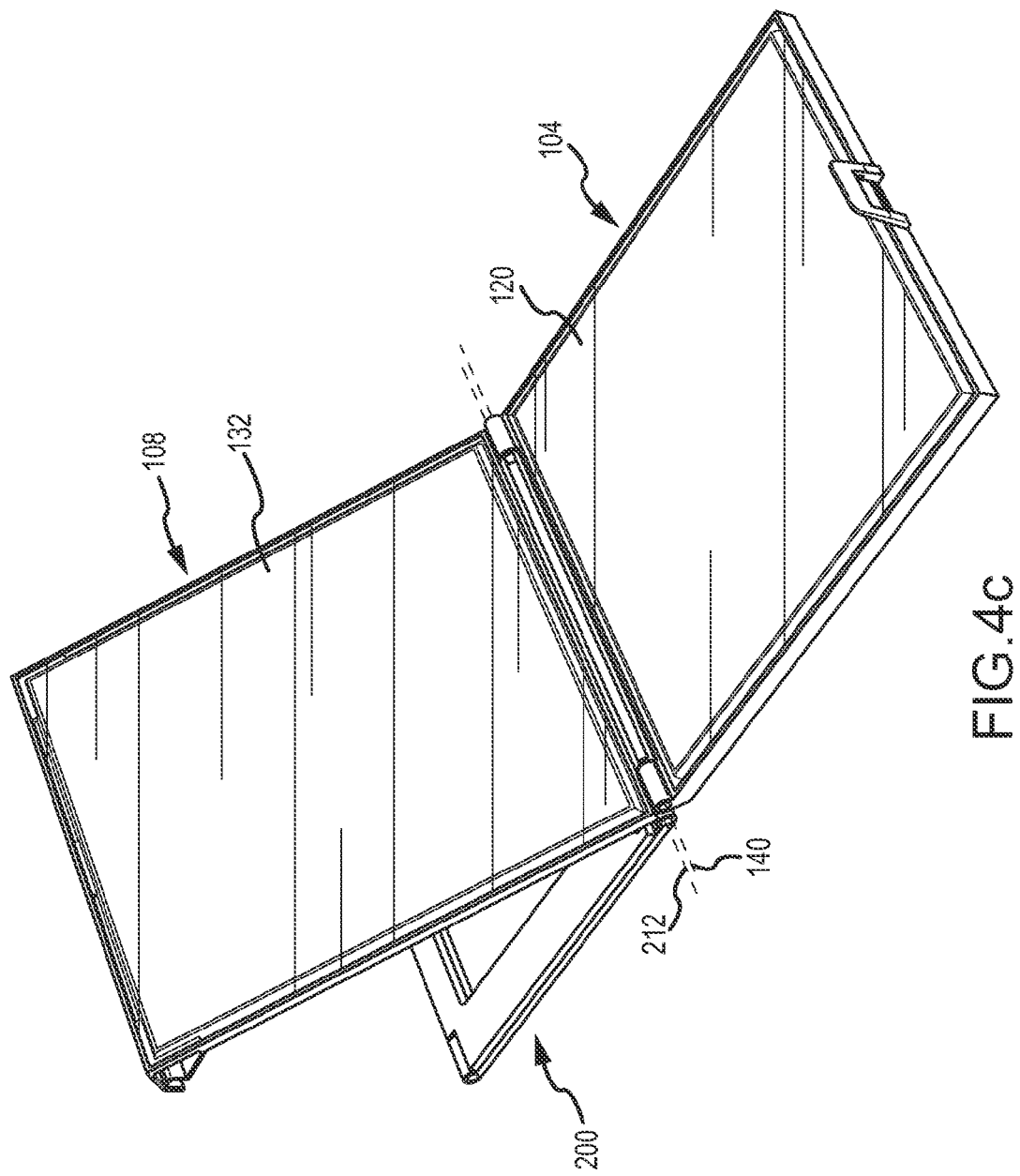
Figure 4D:
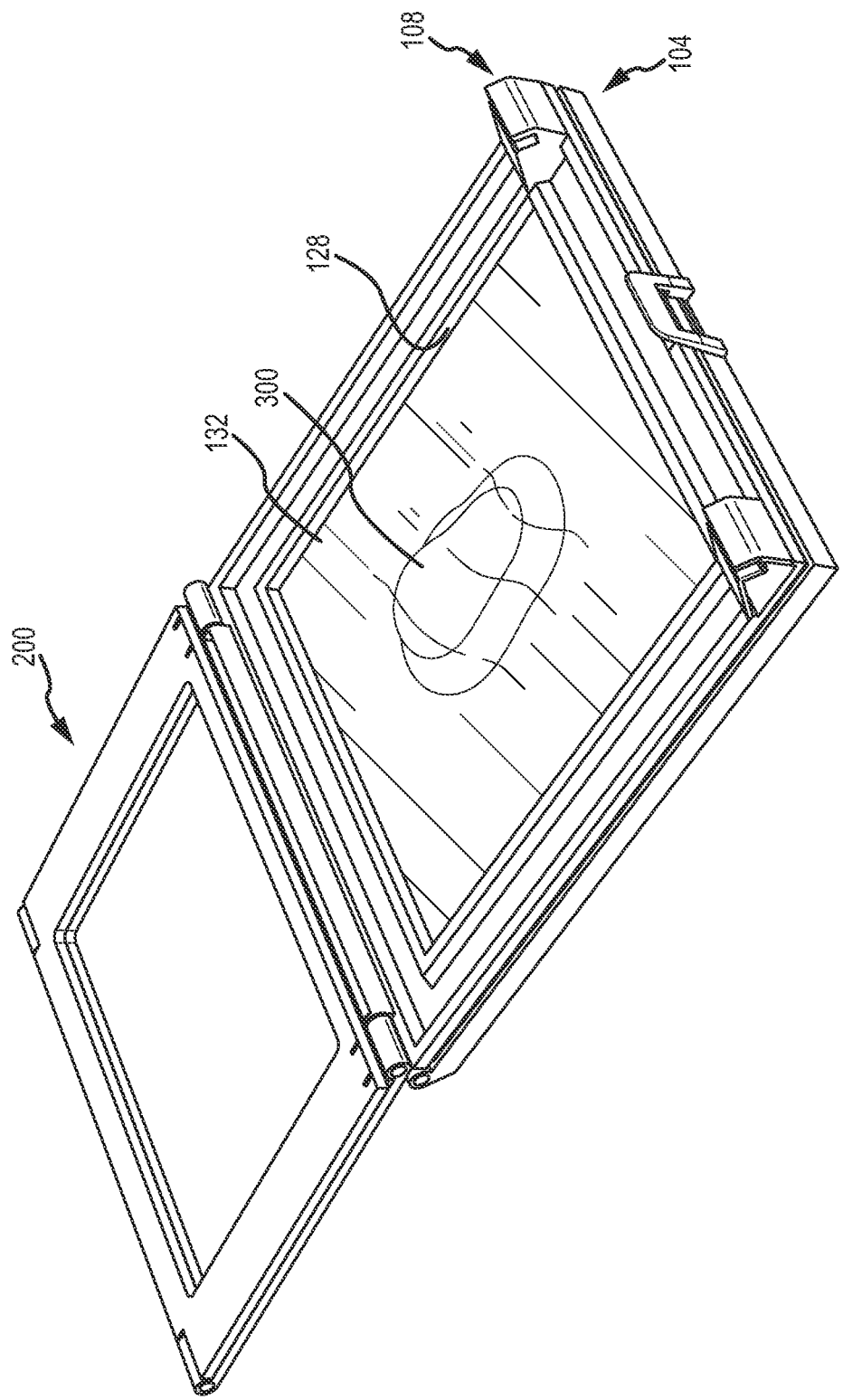
Figure 4E:
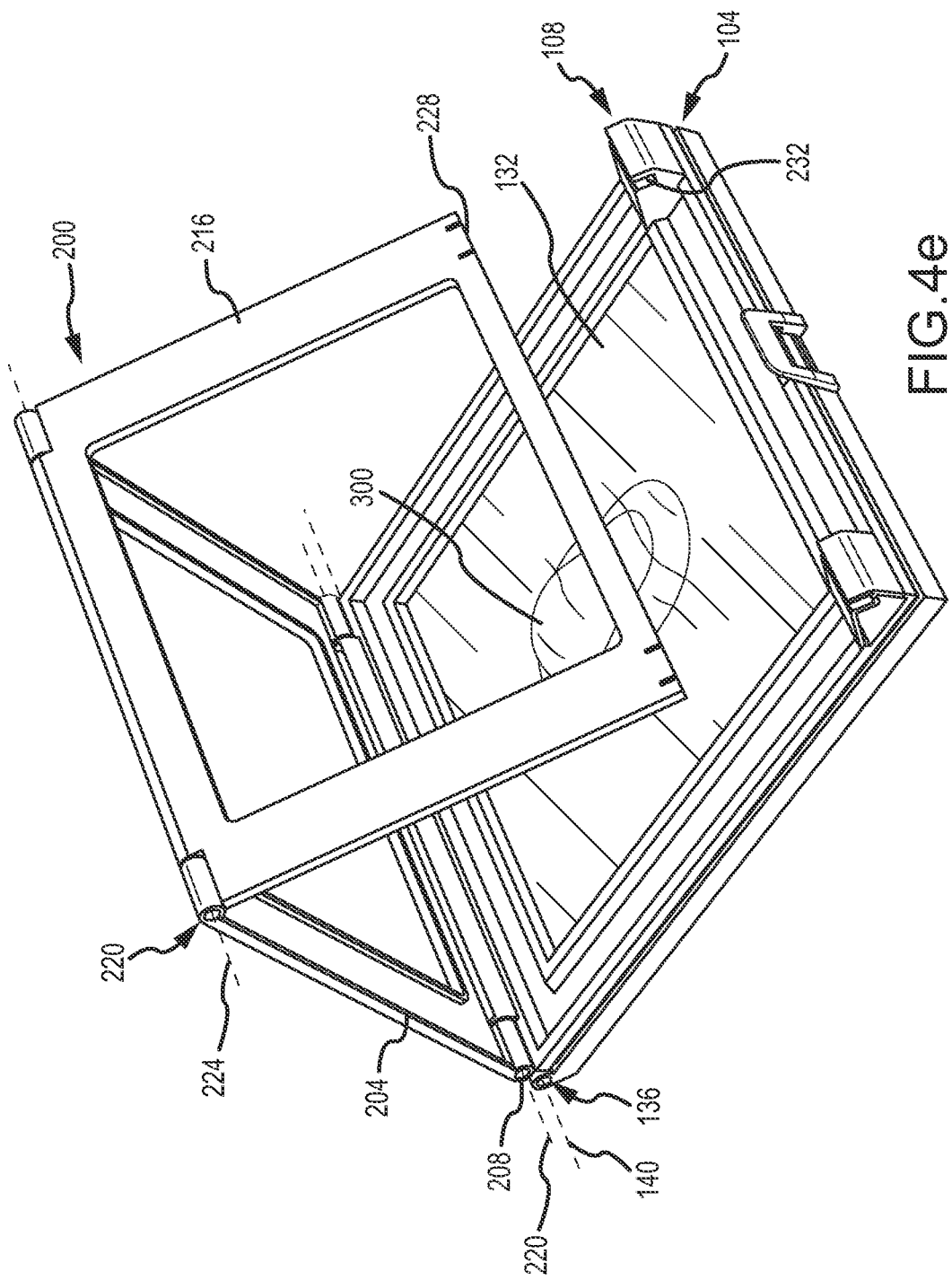
Figure 4F:
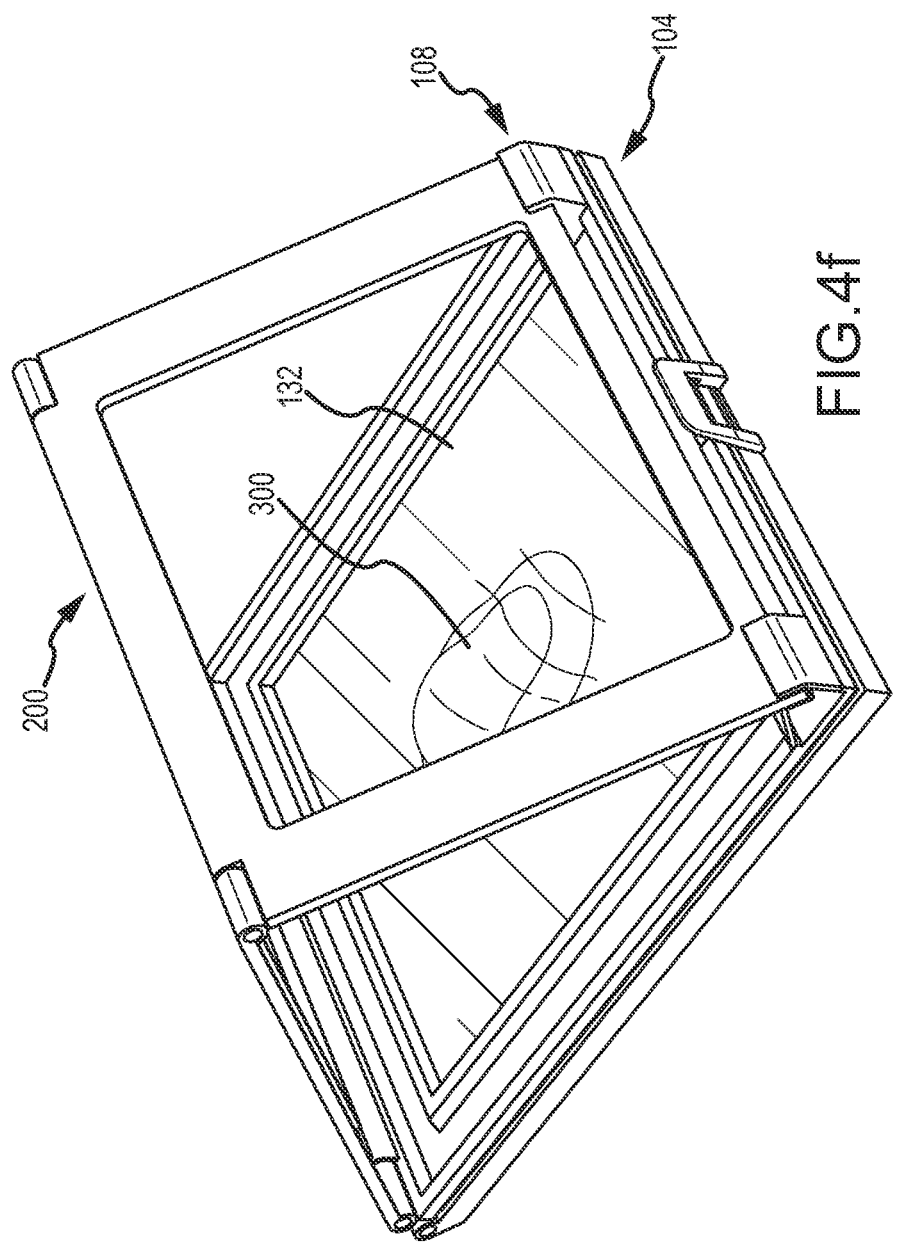

The prop 200 may include at least a first prop member 204 interconnectable to at least one of the first and second positioning members 104, 108. For instance, the first prop member 204 may be fixably positionable relative to at least one of the first and second positioning members 104, 108. In one arrangement, the apparatus 100 may include a second hinge mechanism 208 (see FIG. 4a) disposed adjacent a first location 209 on the second frame member 124 that is configured to allow for pivotal movement between the first prop member 204 and the second frame member 124 about a second pivot axis 212.

For instance, the first prop member 204 and the second frame member 124 may include respective third and fourth hinge elements (not shown) that are secured to or at least partially form the second hinge mechanism 208. The second hinge mechanism 208 may allow for relative positioning between the first prop member 204 and the second frame member 124 between a number of positions, such as between at least a deployed position (as in FIGS. 4f-6b) that allows for imaging of a specimen 300 retained within the apparatus 100 along one or more particular axes through the specimen 300 and a storage position (as in FIG. 4a) whereby the prop 200 is collapsed against the second positioning member 108.

In some arrangements, the prop 200 may also include a second prop member 216 that is interconnectable to the first prop member 204 and that aids the first prop member 204 in positioning the reference plane 196 at the one or more desired angles and/or orientations relative to the support surface. For instance, the first and second prop members 204, 216 may include respective fifth and sixth hinge elements (not shown) that are secured to or at least partially form a third hinge mechanism 220 (labeled in FIG. 4a) that allow for pivotal movement between the first and second prop members 204, 216 about a pivot axis 224 between a number of positions, such as between at least a deployed position (as in FIGS. 4f-6b) that allows for imaging of a specimen 300 retained within the apparatus 100 along one or more particular axes through the specimen 300 and a storage position (as in FIG. 4a) whereby the prop 200 is collapsed against the second positioning member 108.

The second prop member 216 may be removably fixable or at least interconnectable to the second frame member 124 at a second location 226 that is spaced from the first location 209, such as adjacent an opposed end of the second frame member 124. In one arrangement, an end or portion 228 of the second prop member 216 may be removably securable within a correspondingly shaped and sized opening or cavity 232 in the second frame member 124 (e.g., via a press-fit). In this regard, the apparatus 100 may be allowed to assume a substantially robust wedge shape that is operable to substantially automatically position the reference plane 196 at a desired angle and/or orientation relative to the support surface.

In the event that a bottom 240 of opposing top and bottom surfaces 236, 240 of the first prop member 204 is placed on a support surface 252 (see FIGS. 5a-5b), an angle $\alpha$ between the reference place 196 and the support surface may be an acute angle such as 45° or the like. In this regard, a first image (e.g., x-ray image) may be taken along a first axis 256 (shown in FIG. 5b) through the specimen 300 as retained between the first and second sheet members 120, 132. In one arrangement, the first axis 256 may be substantially orthogonal to the support surface 252. As shown in FIG. 5a, the first prop member 204 may have a central opening 260 that is generally aligned or registered with the first and second openings 116, 128 and first and second sheet members 120, 132 of the first and second positioning members 104, 108. In this regard, imaging signals passing through the first and second openings 116, 128 and the first and second sheet members 120, 132 (and a specimen 300 retained therebetween) in a manner that is substantially perpendicular to the support surface 252 (when the bottom surface 240 of the first prop member 204 is resting on the support surface 252) may pass through the central opening 260 and be substantially unencumbered by the body of the first prop member 204. Thus, while the first prop member 204 may be constructed of a low attenuating material (e.g., foam), it may also be constructed of higher attenuating material (e.g., ABS plastic) as imaging signals may pass through the central opening 260 instead of the body of the first prop member 204.

Thereafter, the apparatus 100 may be repositioned or reoriented (e.g., while the specimen 300 continues to be non-movably retained within the apparatus 100) so that a bottom 248 of opposing top and bottom surfaces 244, 248 of the second prop member 216 is disposed against the support surface 252. See FIGS. 6a-6b. For instance, the apparatus 100 may be rotated (e.g., tipped) about the pivot axis 224 (so that the bottom surface 248 is disposed against the support surface 252) and then slid back into the imaging area (or vice versa). In this regard, a second image may be taken along a second axis 264 through the specimen 300 as retained between the first and second sheet members 120, 132, where the first and second image axes 256, 264 are orthogonal (e.g., an angle $\mu$ of 90°).

Similar to the first prop member 204, the second prop member 216 may include a central opening 268 that is also generally aligned or registered with the first and second openings 116, 128 and first and second sheet members 120, 132 of the first and second positioning members 104, 108 so that imaging signals passing through the first and second openings 116, 128 and the first and second sheet members 120, 132 (and a specimen 300 retained therebetween) in a manner that is substantially perpendicular to the support surface 252 (when the bottom surface 248 of the second prop member 216 is resting on the support surface 252) may pass through the central opening 268 and be substantially unencumbered by the body of the second prop member 216. Thus, while the second prop member 216 may be constructed of a low attenuating material (e.g., foam), it may also be constructed of higher attenuating material as imaging signals may pass through the central opening 268 instead of the body of the second prop member 216. In any event, the first and second images can be used to verify tissue margins of the excised tissue specimen 300.

Once tissue margins have been verified, it may be desirable to impart a series of grid lines into a horizontal or flat image of the excised specimen to allow a surgeon to be able to appropriately mark or otherwise indicate where on the specimen a pathologist should focus during subsequent analysis and diagnosis. In this regard, and turning now to FIG. 8a, a grid member 172 (e.g., made of a non or low attenuating material such as foam and/or the like) having a series of radiopaque grid lines 176 across a surface thereof may be configured for insertion into the apparatus 100 so as to float with a tissue specimen placed thereon within the first and second openings 116, 128 as the apparatus 100 is being closed. In one arrangement, the grid member 172 may be sized (e.g., in width and length dimensions, not labeled) for receipt within the first opening 116 of the first positioning member 104.

For instance, the grid member 172 may be rested or placed on top of the first sheet member 120 over the first opening 116; before or after doing so, a tissue specimen 300 may be placed on a top surface of the grid member 172 over the radiopaque grid lines 176 and then the apparatus 100 may be closed via engaging the tab 148 and opening 152 (or other connection/securing components). See FIG. 8b. The apparatus 100 may be positioned flat or horizontally and then tissue specimen 300 may be imaged (e.g., x-rayed) so that the grid lines/indicia appear in the resulting image. The surgeon may then appropriately inform the pathologist the location(s) of the most suspicious areas in the resulting image (e.g., by providing coordinates, marking directly on the image, etc.). The resulting image and excised tissue specimen may then be sent to the pathologist for performing a diagnostic procedure and providing a diagnostic opinion.

Figure 8B:
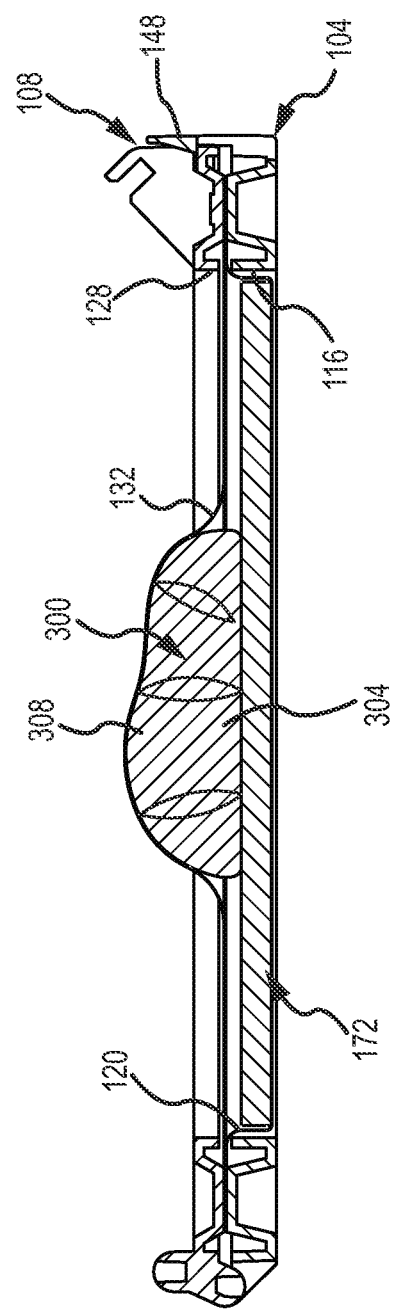
FIG. 8*b* is a cross-sectional view through the apparatus of FIG. 2 with the grid member of FIG. 8*a* and a specimen being secured within the apparatus.

As shown in FIG. 8b, closing of the apparatus 100 results in the second sheet member 132 urging the tissue specimen 300 against the grid member 172 so that the first and second sheet members 120, 132 have respectively at least partially deformed about the grid member 172 and the tissue specimen 300. However, as the grid member 172 is positioned so as to float within the first opening 116 (e.g., as it need not be fixed to the first frame member 112), at least a portion of the load being applied to the grid member 172 (via the second sheet member 132 urging the tissue specimen 300 against the grid member 172) may result in displacement of the grid member 172 downwardly within the first opening 116 relative to the first frame member 112 as opposed to compression of the tissue specimen against the grid member 172. This arrangement advantageously limits large degrees of compression of the tissue specimen and resulting degradations in quality of the resulting images.

Figure 9A:
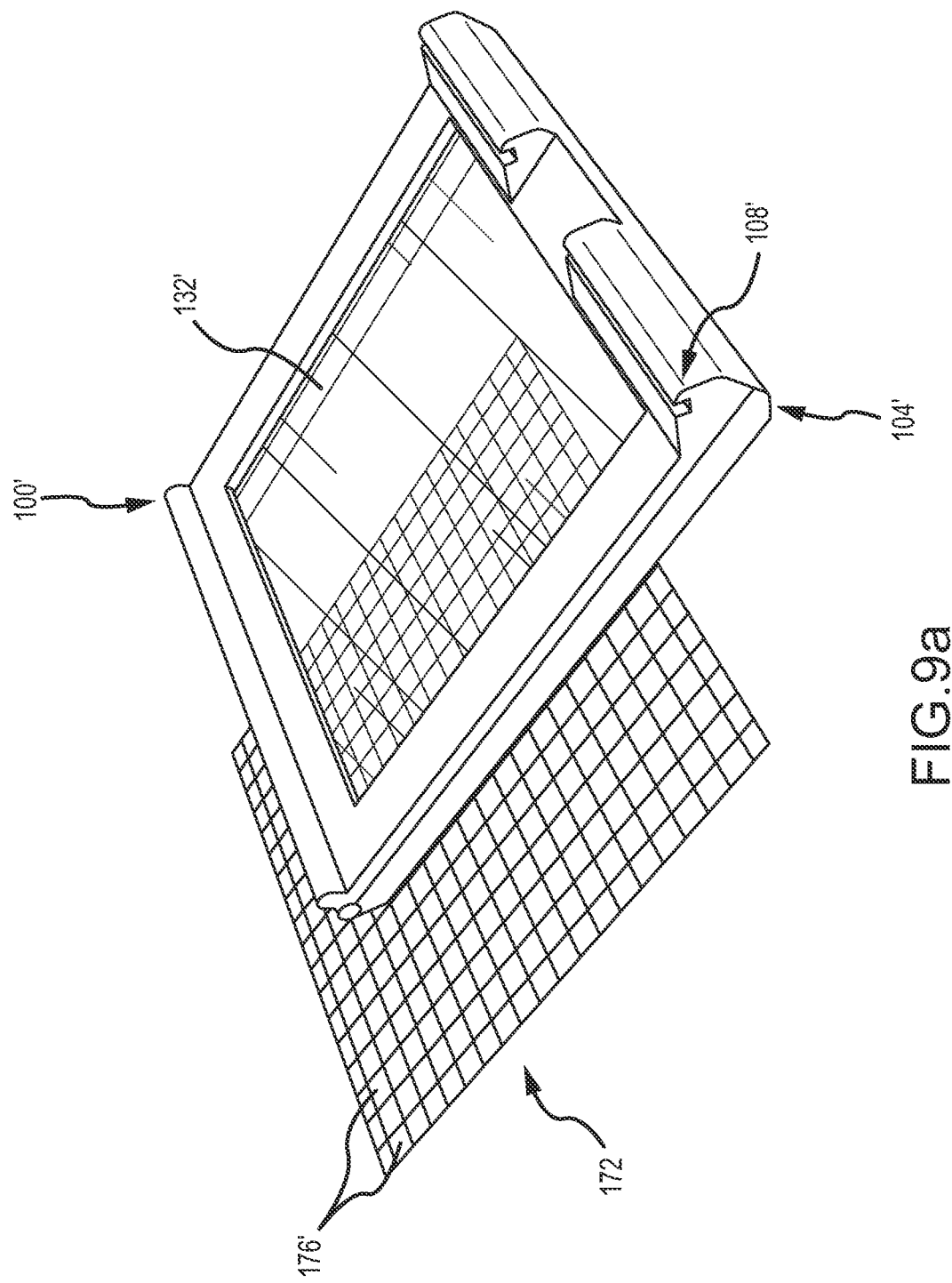
FIG. 9*a* is a perspective view of the specimen holding apparatus similar to that in FIG. 2 but illustrating a removable radiopaque grid member that may be used with the apparatus, according to another embodiment.

FIG. 9a illustrates another embodiment of a grid member 172' that may be removably secured to another embodiment of the apparatus 100', where the grid member 172' includes a series of radiopaque lines 176' thereon configured to impart the grid lines into images of a tissue specimen 300 floatably secured within the apparatus 100'. For instance, the grid member 172' may be inserted or placed into a recess 180 surrounding the first opening 116' in the first frame member 112' so as to contact a support surface 184 of the first frame member 112'. The first frame member 112' may include any appropriate retention member(s) (e.g., snaps, flexible tabs), adhesives, and/or the like to removably retain the grid member 172' within or on the first frame member 112. In any event, propagation of an imaging signal towards and through the first and second openings 116', 128', the first and second sheet members 120', 132', the specimen 300 and the grid member 172' (not necessarily in that order) results in an image of the specimen 300 with the grid lines 176' superimposed thereover for use by radiologists or the like to identify areas of interest in or on the specimen 300.

Figure 9B:
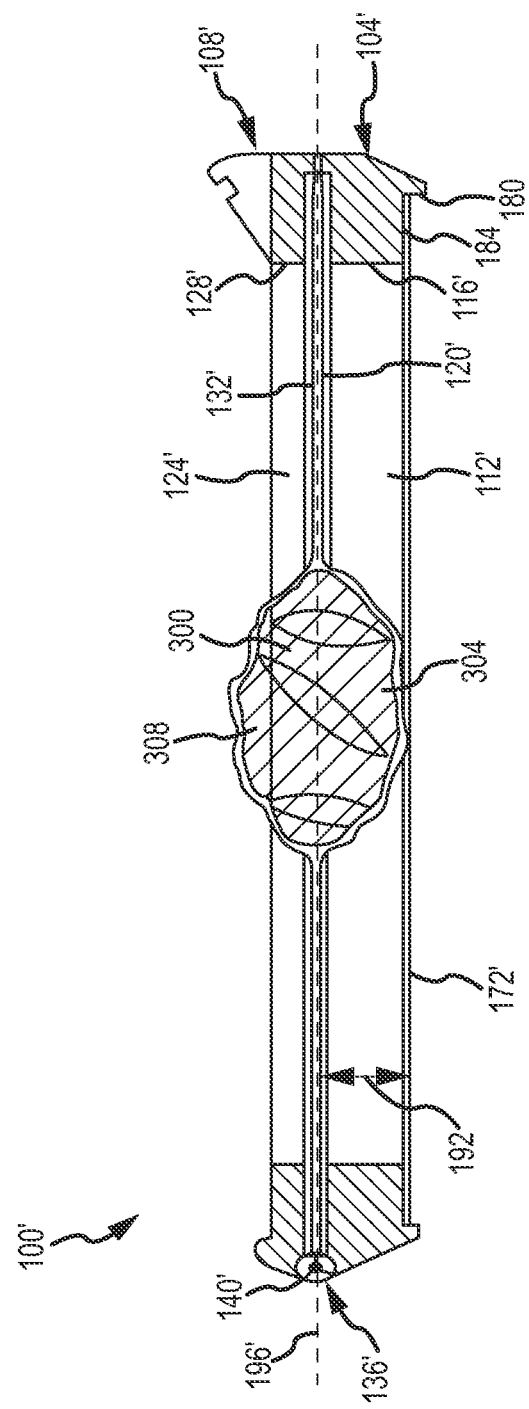
FIG. 9*b* is a cross-sectional view through the apparatus of FIG. 2 with the grid member of FIG. 9*a* and a specimen being secured within the apparatus.

With continued reference to FIG. 9b, the first sheet member 120' and the grid member 172' may be attachable or removably attachable to the first frame member 112' adjacent opposing sides of the first opening 116' so that the first sheet member 120' and the grid member 172' are spaced by a distance 192 (e.g., substantially equal to a height of the first opening 116') when the apparatus 100' is in the closed position. For instance, the distance 192 may be such that upon placement of the specimen 300 into the apparatus 100' and closure of the apparatus 100', the first portion 304 of the specimen 300 may be configured to deform the first sheet member 120' into the first opening 116' and towards the grid member 172' but short of or merely in light or insignificant contact with the grid member 172'. In this regard, the grid member 172' may be configured to impart the grid lines 176' or other coordinate markings into the resulting image in a manner substantially free of deforming the first portion 304 of the specimen 300.

Figure 10:
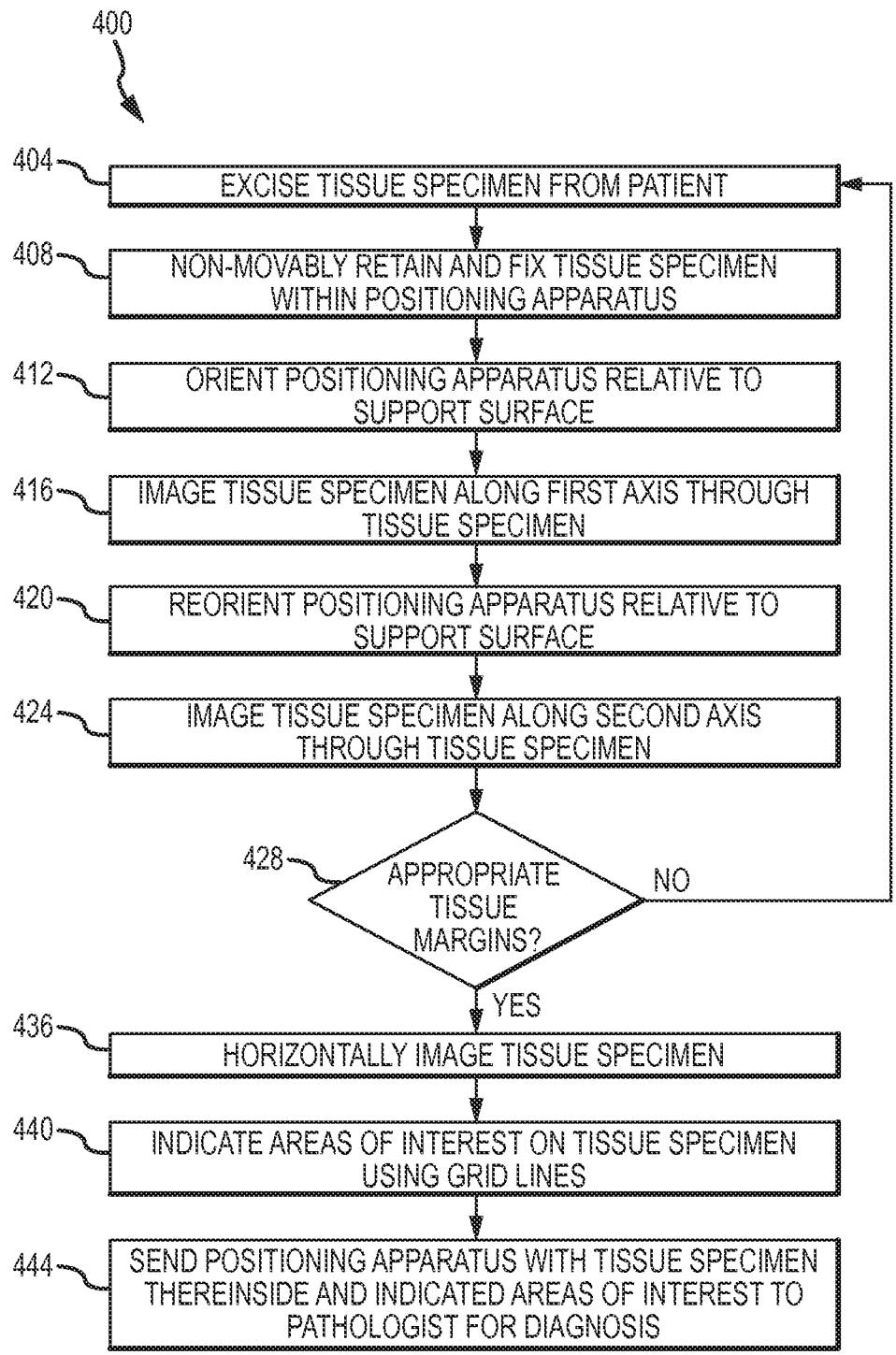
FIG. 10 is a flow diagram illustrating one method for use in tissue abnormality diagnosis.

Turning now to FIG. 10, a flow diagram illustrating one method 400 for use in tissue abnormality diagnosis that may incorporate use of the apparatus 100 is presented. At 404, a surgeon may excise a particular tissue specimen from a patient (e.g., tissue specimen 300 shown in FIG. 3) that is believed to at least partially include cancer and/or one or more other abnormalities. The surgeon, other medical personnel, or machine may then fix 408 the excised tissue specimen within a positioning apparatus (e.g., the apparatus 100). As just one example, the surgeon may pivot the prop 200 away from the apparatus 100 (see FIGS. 4a-4b) and separate the first and second positioning members 104, 108 so as to open the apparatus 100 (which may include overcoming any retention force generated by the retention mechanism 144). See FIG. 4c. Of course, the surgeon may also separate the first and second positioning members 104, 108 without first pivoting the prop 200 away from the apparatus 100. In any event, the surgeon or other personnel may place the specimen 300 on the first sheet member 120 and then close the apparatus 100 to non-movably retain the specimen 300 between the first and second sheet members 120, 132. See FIGS. 3 and 4d.

In addition to securing the specimen 300 between the first and second sheet members 120, 132, the prop 200 of the apparatus 100 may be deployed. In this regard, the surgeon or medical personnel may grasp and pivot the second prop member 216 away from the first prop member 204 to move the end 228 of the second prop member 216 towards the second location 226 on the second frame member 124. See FIG. 4e. The medical personnel may then removably fix or secure the second prop member 216 to the second frame member 124 (e.g., via inserting the end 228 of the second prop member 216 into the opening 232 in the second frame member 124) to assume a deployed position of the prop 200. See FIG. 4f. It is to be understood that the apparatus 100 may be opened for placement of the specimen 300 between the first and second sheet members 120, 132 before or after the prop 200 has been deployed.

The method 400 may also include orienting 412 the positioning apparatus at a first orientation relative to a support surface and then imaging 416 the specimen along a first axis through the specimen to obtain a first image of the specimen. With reference to FIGS. 5a-5b, for instance, the bottom surface 204 of the first prop member 204 may be placed against a support surface 252 and an imaging signal may be propagated through the specimen 300 along a first axis 256 through the specimen 300. In some arrangements, markings or other features may be provided on the support surface 252 that may be used to automatically align the imaging signal with the first and second openings 116, 128 and first and second sheet members 120, 132 of the first and second positioning members 104, 108, the specimen 300, and the central opening 260 of the first prop member 204.

The method 400 may then include reorienting 420 the positioning apparatus relative to the support surface and then imaging 424 the specimen along a second axis through the specimen to obtain a second image of the specimen. For instance, the entire apparatus 100 may be pivoted about the pivot axis 224 (see FIG. 6a-6b) so as to place the bottom surface 248 of the second prop member 216 on the support surface 252 (which may include aligning the bottom surface 248 with any markings or the like on the support surface 252), and an imaging signal may be propagated through the specimen 300 along a second axis 264 through the specimen 260. For instance, the first and second axes 256, 264 may be orthogonal to each other (or disposed at another appropriate angle to each other). Advantageously, the specimen 300 may remain substantially fixed or non-movable within the apparatus during the reorienting 420 (e.g., due at least in part to the first and second elastically deformable sheet members) to increase the accuracy of subsequent imaging operations and analysis. In one arrangement, the specimen 300 may also be substantially non-deformably retained within the apparatus (e.g., retained in a manner substantially free of experiencing changes to its natural shape and dimensions) to further increase the accuracy of subsequent imaging operations and analysis.

Returning to FIG. 10, the method 400 may query 428 whether appropriate tissue margins have been detected in the specimen 300. For instance, a surgeon or radiologist may examine both of the first and second images to confirm that any appropriate tissue margins have been satisfied (e.g., whether any appropriate tissue margins surround the area(s) of interest within the specimen 300). In response to a negative answer to the query at 428, the method 400 may flow back to 404 to excise another tissue specimen, retain and fix 408 the specimen within a positioning apparatus, and the like.

In the event that the tissue margins have been verified at 428, the method 400 may include horizontally (e.g., so that the reference plane 196 is substantially parallel to the support surface 252) imaging 436 the specimen through any appropriate grid member (which may entail appropriately aligning the apparatus 100 with any appropriate markings or the like on/near the support surface 252). For instance, the first and second positioning members 104, 108 may be separated, the specimen 300 may be removed, the grid member 172 of FIG. 8a may be placed onto the first sheet member 120 over the first opening 116, the specimen 300 may be placed onto the grid member 172, and then the apparatus 100 may be closed to at least partially deform the first and second sheet members 120, 132 about the grid member 172 and specimen 300, respectively, and non-movably secure the same within the apparatus 100. See FIG. 8a. The apparatus 100 may then be placed flat or horizontal and imaged to obtain one or more images having grid lines imparted therein for use by the surgeon, a pathologist, etc.

Figure 7B:
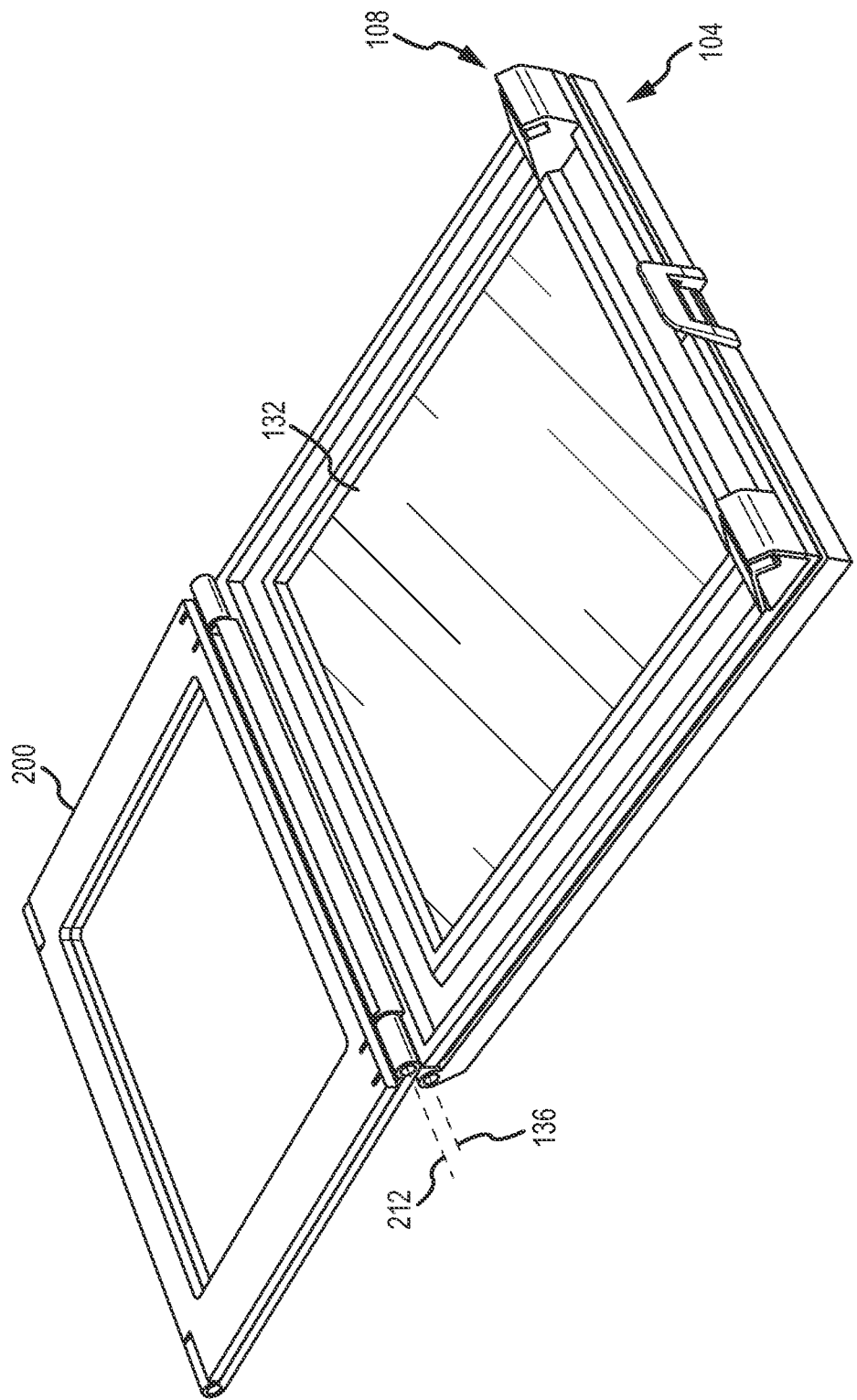

In some arrangements, the prop 200 may be removed from the first and second positioning members 104, 108 before horizontally imaging the specimen (e.g., to avoid possible interference with the imaging signal, to render the apparatus more easily manageable, and/or the like). For instance, the end 228 of the second prop member 216 may be separated from the second positioning member 108 (e.g., see FIG. 7a, the specimen 300 not shown) and the second prop member 216 may be folded against or pivoted (e.g., about axis 224) towards the first prop member 204 (e.g., see FIG. 7b, the specimen 300 not shown). The entire prop 200 may then be appropriately separated from the first and second positioning members 104, 108. In one arrangement, a user may grasp and pull the prop 200 away from the second positioning member 108 (e.g., so as to separate the third and fourth hinge elements of the second hinge mechanism 208) so as to separate the prop 200 from the second positioning member 108. In another arrangement, the prop 200 may be designed to break-away from the second positioning member 108 when pivoted about the pivot axis 212 away from the second positioning member 108 more than a particular amount. In a further arrangement, the prop 200 may remain connected to the first and/or second positioning members 104, 108 but may be pivoted (e.g., about pivot axis 208) out of the imaging zone before the specimen 300 is horizontally imaged (e.g., as in FIG. 7b).

After obtaining the horizontal image of the specimen at 436, the method 400 may include indicating 440 areas of interest on the specimen using the grid lines present in the resulting horizontal image. For instance, the surgeon and/or radiologist may examine the resulting horizontal image and highlight and/or write down those grid line coordinates associated with areas of interest. The positioning apparatus with the specimen retained thereinside (e.g., in substantially the same position/orientation within the apparatus as when the specimen was first placed into the apparatus, e.g., at step 408) and the indicated areas of interest (e.g., directly on the resulting horizontal image and/or the like) may then be sent to a pathologist or the like for diagnosis of the specimen. As the specimen may remain in substantially the same position/orientation relative to the grid member from the time of horizontal imaging up to and including diagnosis by the pathologist (e.g., due to the first and second positioning members 104, 108 as discussed previously), which may include transport of the apparatus from a first location to a second location, a substantially high correspondence between areas of interest identified on the resulting horizontal image and corresponding areas on the actual specimen may be obtained leading to greater accuracy of cancer and/or other tissue abnormality diagnosis.

The various components of the apparatus 100 may be constructed of any appropriate materials consistent with their functionalities disclosed herein and/or any other functionalities flowing from a reading of the present disclosure. The first and second sheet members 120, 132 may be constructed of radiolucent materials such as plastic films and the like. Furthermore, the first and second sheet members 120, 132 may each have a modulus of elasticity selected to impart any desired degree of holding or retaining of the specimen 300 within the apparatus 100. As discussed previously, the modulus of elasticity and/or other properties of the first and second sheet members 120, 132 may be selected to non-movably retain the specimen 300 with the apparatus 100 while precluding or limiting deformation of the specimen 300 by the first and second sheet members 120, 132. The grid member 172 may be constructed of both radiolucent and radiopaque materials/components (e.g., where the grid member 172 is constructed of a substantially planar radiolucent member including a series of radiopaque grid lines formed on a surface thereof).

While the first and second frame members 112, 124 and the first and second prop members 204, 216 may be constructed of any appropriate low attenuating material (e.g., foam or the like) to reduce any negative impacts on resulting images of a specimen retained within the apparatus 100, such need not necessarily be the case. For instance, and with reference to FIGS. 9a-9b, imaging signals may be configured to pass through the first and second sheet members 120, 132 and the specimen 300 (e.g., along axes 256) in a manner that is substantially perpendicular to the support surface 252 and only within an "imaging zone" generally defined by imaginary reference planes extending generally perpendicularly away from an inner perimeter of the central opening 260 of the first prop member 204. As can be appreciated from FIGS. 5a-5b, such reference planes would also substantially intersect an inner perimeter of the first and second openings 116, 128 of the first and second positioning members 104, 108. A corresponding imaging zone may be defined for other orientations of the apparatus 100 (e.g., the orientation of FIGS. 6a-6b).

In the case of horizontal imaging of a specimen 300 retained within the apparatus 100, the imaging zone could be defined by imaginary reference planes extending generally perpendicularly away from an inner perimeter of the first opening 116 of the first positioning member 104 so as to substantially intersect with an inner perimeter of the second opening 128 of the second positioning member 108. So long as the imaging signals are propagated substantially within the particular imaging zone, any attenuation of the imaging signals due to the particular materials of the first and second positioning members 104, 108 and/or the first and second prop members 204, 216 can be avoided or at least limited. It is envisioned that the first and second positioning members 104, 108 and the first and second prop members 204, 216 can be constructed of materials such as ABS plastic, foam, and/or the like.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. For instance, while the disclosed apparatus 100 has been primarily discussed in the context of x-ray imaging, it is envisioned that the apparatus 100 could also be used to non-movably hold and retain a specimen for other types of imaging operations (e.g., ultrasound imaging). Furthermore, while the apparatus 100 has primarily been disclosed for use with tissue specimens 300, it is envisioned that the apparatus 100 could also be used with other types of specimens (e.g., non-living specimens).

Still further, it is envisioned that apparatus could be used to quickly and efficiently obtain angles and orientations between the reference plane and the support surface other than those specifically disclosed herein depending upon the particular application. For instance, in the event that the prop 200 is configured to position the reference plane 196 at an angle other than 45° relative to a support surface, then the first and second axes 256, 264 along which first and second images are taken with the apparatus 100 in the respective first and second orientations of FIGS. 5a-5b and 6a-6b may be other than orthogonal (e.g., 60° or 120° apart).

In one arrangement, a somewhat rigid radiolucent layer or board may be secured within the recess 180 surrounding the first opening 116' in the apparatus 100' of FIGS. 9a-9b (e.g., in addition to or as an alternative to the grid member 172'). In this regard, while the second sheet member 132' may continue to at least substantially non-deformably retain the second portion 308 of the specimen 300, the somewhat rigid layer (e.g., more rigid than the first and second sheet members 120', 132') may serve to deformably or compressibly retain the first portion 304 of the specimen. In one arrangement, the grid member 172' may then be secured within the recess 180 so as to be at least partially spaced from the somewhat rigid layer in the area over the specimen 300. In another arrangement, the grid member 172' may be designed to be at least somewhat rigid and to at least partially protrude into the first cavity 116' towards the specimen 300 so as to compress at least partially compress the specimen 300.

It is noted that at least some of the gaps illustrated in FIG. 9b (and/or in other figures), such as between the first and second sheet members 120', 132' and the first and second frame members 112,' 124' have been provided in the interest of clarity and that such gaps may not actually exist in reality. Furthermore, it is noted that use of "first," "second," "third," etc. herein (e.g., "first recess," "second recess," "third recess," etc.) and the like does not necessarily connote any specific number of features or components in the disclosed apparatus 100. Rather, such labels have merely been used to differentiate among a number of common features (e.g., to differentiate among a number of recesses of the apparatus 100).

While this disclosure contains many specifics, these should not be construed as limitations on the scope of the disclosure or of what may be claimed, but rather as descriptions of features specific to particular embodiments of the disclosure. Certain features that are described in this specification in the context of separate embodiments and/or arrangements can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. An apparatus for positionably retaining a tissue specimen, comprising:
    a first positioning member comprising a first frame member and a first at least partially elastically deformable sheet member, wherein the first frame member defines a first opening therein, and wherein the first sheet member is interconnected to the first frame member and spans the first opening; and
    a second positioning member comprising a second frame member and a second at least partially elastically deformable sheet member, wherein the second frame member defines a second opening therein, wherein the second sheet member is interconnected to the second frame member and spans the second opening, and wherein the first frame member and second frame member are positionable to allow the first and second sheet members to elastically deform about opposite portions of a tissue specimen to retain the tissue specimen therebetween and suspend the tissue specimen within the first and second openings when the first and second frame members are fixedly positioned relative to each other.

2. The apparatus of claim 1, wherein the first positioning member comprises a first connection member, wherein the second positioning member comprises a second connection member, and wherein the first and second connection members are removably connectable to fixedly position the first and second frame members relative to each other.

3. The apparatus of claim 2, wherein the first positioning member comprises a first hinge element, wherein the second positioning member comprises a second hinge element, and wherein the first and second hinge elements are pivotable for relative positioning between the first and second sheet members between at least an opening position that allows for placement of the tissue specimen between the first and second sheet members and a closed position that holds the tissue specimen between the first and second sheet members.

4. The apparatus of claim 3, further comprising:
a grid member comprising a series of at least partially radiopaque grid lines across at least one surface thereof, wherein the grid member is removably positionable across at least a portion of the first opening.

5. The apparatus of claim 1, further comprising:
a reference plane extending between the first and second sheet members when the first and second positioning members are fixably positioned relative to each other; and
a prop extendable from at least one of the first and second positioning members, wherein the prop is positionable on a support surface, and wherein the prop is configured to position the reference plane at one or more desired angles or orientations relative to the support surface.

6. The apparatus of claim 5, wherein the prop is removably attachable to at least one of the first and second positioning members, wherein the reference plane is parallelly positionable to the support surface when the prop is removed from the at least one of the first and second frame members to facilitate substantially flat imaging of the tissue specimen.

7. The apparatus of claim 5, wherein the prop comprises a first hinge element, wherein one of the first and second positioning members comprises a second hinge element, and wherein the first and second hinge elements are pivotally interconnectable for movable positioning of the prop relative to the one of the first and second positioning members.

8. The apparatus of claim 5, adapted for use with an imaging signal, wherein each of the first and second sheet members is configured to at least partially transmit said imaging signal therethrough.

9. The apparatus of claim 1, wherein the first frame member and second frame member are positionable to allow the first and second sheet members to elastically deform about opposite portions of the tissue specimen to retain the tissue specimen therebetween and suspend the tissue specimen within the first and second openings when the first and second frame members are fixedly positioned relative to each other substantially free of deforming the tissue specimen.

10. The apparatus of claim 1, wherein the first and second sheet members are constructed of a common material.

11. The apparatus of claim 10, wherein the common material is a polyurethane film.

12. The apparatus of claim 1, wherein the first sheet member includes a first thickness, wherein the second sheet member includes a second thickness, and wherein the first and second thicknesses are equal.

13. An apparatus for use in positionably retaining a tissue specimen, comprising:
a first positioning member comprising a first frame member and a first imaging zone through a first cavity of the first frame member;
a second positioning member comprising a second frame member and a second imaging zone through a second cavity of the second frame member, wherein the first and second frame members are fixably positionable to allow the first and second imaging zones to hold a tissue specimen therebetween;
a reference plane extending between the first and second positioning members when the first and second positioning members are fixably positioned relative to each other, wherein the first imaging zone includes a first at least partially elastically deformable member, wherein the second imaging zone includes a second at least partially elastically deformable member, wherein the first and second elastically deformable members are respectively configured to deform and first and second portions of the tissue specimen and the first and second cavities are respectively configured to receive the first and second portions of the tissue specimen when first and second frame members are fixedly positioned relative to each other; and
a prop extendable from at least one of the first and second positioning members, wherein the prop is positionable on a support surface, and wherein the prop is configured to supportably position the reference plane at one or more desired angles or orientations relative to the support surface.

14. The apparatus of claim 13, wherein the prop includes at least a first prop member that is interconnectable to at least one of the first and second positioning members.

15. The apparatus of claim 14, wherein the prop is adapted so that the first prop member is fixably positionable relative to at least one of the first and second positioning members.

16. The apparatus of claim 15, wherein the prop includes a second prop member interconnectable to the first prop member.

17. The apparatus of claim 16, wherein the first and second prop members are angularly positionable for relative positioning of the reference plane at the one or more desired angles or orientations relative to the support surface.

18. The apparatus of claim 16, wherein the first prop member is interconnectable to one of the first and second positioning members at a first location, wherein the second prop member is interconnectable to one of the first and second positioning members at a second location, and wherein the first location is spaced from the second location.

19. The apparatus of claim 13, wherein the prop is movably positionable relative to at least one of the first and second positioning members.

20. The apparatus of claim 13, wherein the prop is collapsible against at least one of the first and second frame members to facilitate storage of the apparatus.

* * * * *